United States Patent [19]
Lambert, Jr.

[11] Patent Number: 5,912,228
[45] Date of Patent: Jun. 15, 1999

[54] THERAPEUTIC COMPOSITIONS COMPRISING BACTERICIDAL/PERMEABILITY-INCREASING (BPI) PROTEIN PRODUCTS

[75] Inventor: Lewis H. Lambert, Jr., Fremont, Calif.

[73] Assignee: XOMA Corporation, Berkeley, Calif.

[21] Appl. No.: 08/586,133

[22] Filed: Jan. 12, 1996

Related U.S. Application Data

[63] Continuation-in-part of application No. 08/530,599, Sep. 19, 1995, abandoned, which is a continuation-in-part of application No. 08/372,104, Jan. 13, 1995, abandoned.

[51] Int. Cl.$^6$ ............................. A61K 38/17; C07K 14/47
[52] U.S. Cl. ............................................. 514/12; 530/350
[58] Field of Search ................................ 514/12; 530/350

[56] References Cited

U.S. PATENT DOCUMENTS

| | | | |
|---|---|---|---|
| 5,447,913 | 9/1995 | Ammons et al. | 514/12 |
| 5,488,034 | 1/1996 | McGregor et al. | 514/12 |
| 5,578,572 | 11/1996 | Horwitz et al. | 514/12 |

*Primary Examiner*—Kawai Lau
*Attorney, Agent, or Firm*—McAndrews, Held & Malloy, Ltd.

[57] ABSTRACT

Improved therapeutic compositions having enhanced antimicrobial activity comprising a bactericidal/permeability-increasing (BPI) protein product and an bactericidal-activity enhancing polyoxyethylene block copolymer surfactant (poloxamer) surfactant or a bacterial and fungal growth-inhibiting enhancing poloxamer surfactant, optionally with EDTA, and methods for treating bacterial infection by administering such compositions, alone or concurrently with antibiotics.

6 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1813 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 31..1491

(ix) FEATURE:
      (A) NAME/KEY: mat_peptide
      (B) LOCATION: 124..1491

(ix) FEATURE:
      (A) NAME/KEY: misc_feature
      (D) OTHER INFORMATION: "rBPI"

(xi) SEQUENCE DESCRIPTION: SEQ ID NO:1:

```
CAGGCCTTGA GGTTTTGGCA GCTCTGGAGG ATG AGA GAG AAC ATG GCC AGG GGC        54
                                Met Arg Glu Asn Met Ala Arg Gly
                                -31 -30                     -25

CCT TGC AAC GCG CCG AGA TGG GTG TCC CTG ATG GTG CTC GTC GCC ATA       102
Pro Cys Asn Ala Pro Arg Trp Val Ser Leu Met Val Leu Val Ala Ile
            -20             -15                 -10

GGC ACC GCC GTG ACA GCG GCC GTC AAC CCT GGC GTC GTG GTC AGG ATC       150
Gly Thr Ala Val Thr Ala Ala Val Asn Pro Gly Val Val Val Arg Ile
        -5                   1               5

TCC CAG AAG GGC CTG GAC TAC GCC AGC CAG CAG GGG ACG GCC GCT CTG       198
Ser Gln Lys Gly Leu Asp Tyr Ala Ser Gln Gln Gly Thr Ala Ala Leu
 10              15                  20                      25

CAG AAG GAG CTG AAG AGG ATC AAG ATT CCT GAC TAC TCA GAC AGC TTT       246
Gln Lys Glu Leu Lys Arg Ile Lys Ile Pro Asp Tyr Ser Asp Ser Phe
             30                  35                  40

AAG ATC AAG CAT CTT GGG AAG GGG CAT TAT AGC TTC TAC AGC ATG GAC       294
Lys Ile Lys His Leu Gly Lys Gly His Tyr Ser Phe Tyr Ser Met Asp
                 45                  50                  55

ATC CGT GAA TTC CAG CTT CCC AGT TCC CAG ATA AGC ATG GTG CCC AAT       342
Ile Arg Glu Phe Gln Leu Pro Ser Ser Gln Ile Ser Met Val Pro Asn
```

|  |  | 60 |  |  | 65 |  |  | 70 |  |  |  |
|---|---|---|---|---|---|---|---|---|---|---|---|
| GTG | GGC | CTT | AAG | TTC | TCC | ATC | AGC | AAC | GCC | AAT | ATC | AAG | ATC | AGC | GGG | 390 |
| Val | Gly | Leu | Lys | Phe | Ser | Ile | Ser | Asn | Ala | Asn | Ile | Lys | Ile | Ser | Gly |  |
|  |  | 75 |  |  | 80 |  |  | 85 |  |  |  |

```
GTG GGC CTT AAG TTC TCC ATC AGC AAC GCC AAT ATC AAG ATC AGC GGG      390
Val Gly Leu Lys Phe Ser Ile Ser Asn Ala Asn Ile Lys Ile Ser Gly
             75              80              85

AAA TGG AAG GCA CAA AAG AGA TTC TTA AAA ATG AGC GGC AAT TTT GAC      438
Lys Trp Lys Ala Gln Lys Arg Phe Leu Lys Met Ser Gly Asn Phe Asp
 90              95             100                         105

CTG AGC ATA GAA GGC ATG TCC ATT TCG GCT GAT CTG AAG CTG GGC AGT      486
Leu Ser Ile Glu Gly Met Ser Ile Ser Ala Asp Leu Lys Leu Gly Ser
                 110             115             120

AAC CCC ACG TCA GGC AAG CCC ACC ATC ACC TGC TCC AGC TGC AGC AGC      534
Asn Pro Thr Ser Gly Lys Pro Thr Ile Thr Cys Ser Ser Cys Ser Ser
             125             130             135

CAC ATC AAC AGT GTC CAC GTG CAC ATC TCA AAG AGC AAA GTC GGG TGG      582
His Ile Asn Ser Val His Val His Ile Ser Lys Ser Lys Val Gly Trp
             140             145             150

CTG ATC CAA CTC TTC CAC AAA AAA ATT GAG TCT GCG CTT CGA AAC AAG      630
Leu Ile Gln Leu Phe His Lys Lys Ile Glu Ser Ala Leu Arg Asn Lys
155             160             165

ATG AAC AGC CAG GTC TGC GAG AAA GTG ACC AAT TCT GTA TCC TCC AAG      678
Met Asn Ser Gln Val Cys Glu Lys Val Thr Asn Ser Val Ser Ser Lys
170             175             180             185

CTG CAA CCT TAT TTC CAG ACT CTG CCA GTA ATG ACC AAA ATA GAT TCT      726
Leu Gln Pro Tyr Phe Gln Thr Leu Pro Val Met Thr Lys Ile Asp Ser
                 190             195             200

GTG GCT GGA ATC AAC TAT GGT CTG GTG GCA CCT CCA GCA ACC ACG GCT      774
Val Ala Gly Ile Asn Tyr Gly Leu Val Ala Pro Pro Ala Thr Thr Ala
             205             210             215

GAG ACC CTG GAT GTA CAG ATG AAG GGG GAG TTT TAC AGT GAG AAC CAC      822
Glu Thr Leu Asp Val Gln Met Lys Gly Glu Phe Tyr Ser Glu Asn His
             220             225             230

CAC AAT CCA CCT CCC TTT GCT CCA CCA GTG ATG GAG TTT CCC GCT GCC      870
His Asn Pro Pro Pro Phe Ala Pro Pro Val Met Glu Phe Pro Ala Ala
             235             240             245

CAT GAC CGC ATG GTA TAC CTG GGC CTC TCA GAC TAC TTC TTC AAC ACA      918
His Asp Arg Met Val Tyr Leu Gly Leu Ser Asp Tyr Phe Phe Asn Thr
250             255             260             265

GCC GGG CTT GTA TAC CAA GAG GCT GGG GTC TTG AAG ATG ACC CTT AGA      966
Ala Gly Leu Val Tyr Gln Glu Ala Gly Val Leu Lys Met Thr Leu Arg
                 270             275             280

GAT GAC ATG ATT CCA AAG GAG TCC AAA TTT CGA CTG ACA ACC AAG TTC     1014
Asp Asp Met Ile Pro Lys Glu Ser Lys Phe Arg Leu Thr Thr Lys Phe
             285             290             295

TTT GGA ACC TTC CTA CCT GAG GTG GCC AAG AAG TTT CCC AAC ATG AAG     1062
Phe Gly Thr Phe Leu Pro Glu Val Ala Lys Lys Phe Pro Asn Met Lys
             300             305             310

ATA CAG ATC CAT GTC TCA GCC TCC ACC CCG CCA CAC CTG TCT GTG CAG     1110
Ile Gln Ile His Val Ser Ala Ser Thr Pro Pro His Leu Ser Val Gln
315             320             325

CCC ACC GGC CTT ACC TTC TAC CCT GCC GTG GAT GTC CAG GCC TTT GCC     1158
Pro Thr Gly Leu Thr Phe Tyr Pro Ala Val Asp Val Gln Ala Phe Ala
330             335             340             345

GTC CTC CCC AAC TCC TCC CTG GCT TCC CTC TTC CTG ATT GGC ATG CAC     1206
Val Leu Pro Asn Ser Ser Leu Ala Ser Leu Phe Leu Ile Gly Met His
             350             355             360

ACA ACT GGT TCC ATG GAG GTC AGC GCC GAG TCC AAC AGG CTT GTT GGA     1254
Thr Thr Gly Ser Met Glu Val Ser Ala Glu Ser Asn Arg Leu Val Gly
             365             370             375

GAG CTC AAG CTG GAT AGG CTG CTC CTG GAA CTG AAG CAC TCA AAT ATT     1302
Glu Leu Lys Leu Asp Arg Leu Leu Leu Glu Leu Lys His Ser Asn Ile
```

```
                380              385              390
GGC CCC TTC CCG GTT GAA TTG CTG CAG GAT ATC ATG AAC TAC ATT GTA    1350
Gly Pro Phe Pro Val Glu Leu Leu Gln Asp Ile Met Asn Tyr Ile Val
    395              400              405

CCC ATT CTT GTG CTG CCC AGG GTT AAC GAG AAA CTA CAG AAA GGC TTC    1398
Pro Ile Leu Val Leu Pro Arg Val Asn Glu Lys Leu Gln Lys Gly Phe
410              415              420              425

CCT CTC CCG ACG CCG GCC AGA GTC CAG CTC TAC AAC GTA GTG CTT CAG    1446
Pro Leu Pro Thr Pro Ala Arg Val Gln Leu Tyr Asn Val Val Leu Gln
                430              435              440

CCT CAC CAG AAC TTC CTG CTG TTC GGT GCA GAC GTT GTC TAT AAA        1491
Pro His Gln Asn Phe Leu Leu Phe Gly Ala Asp Val Val Tyr Lys
            445              450              455

TGAAGGCACC AGGGGTGCCG GGGGCTGTCA GCCGCACCTG TTCCTGATGG GCTGTGGGGC  1551

ACCGGCTGCC TTTCCCCAGG GAATCCTCTC CAGATCTTAA CCAAGAGCCC CTTGCAAACT  1611

TCTTCGACTC AGATTCAGAA ATGATCTAAA CACGAGGAAA CATTATTCAT TGGAAAAGTG  1671

CATGGTGTGT ATTTTAGGGA TTATGAGCTT CTTTCAAGGG CTAAGGCTGC AGAGATATTT  1731

CCTCCAGGAA TCGTGTTTCA ATTGTAACCA AGAAATTTCC ATTTGTGCTT CATGAAAAAA  1791

AACTTCTGGT TTTTTTCATG TG                                          1813

(2) INFORMATION FOR SEQ ID NO:2:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Glu Asn Met Ala Arg Gly Pro Cys Asn Ala Pro Arg Trp Val
-31 -30              -25              -20

Ser Leu Met Val Leu Val Ala Ile Gly Thr Ala Val Thr Ala Ala Val
-15              -10               -5                            1

Asn Pro Gly Val Val Arg Ile Ser Gln Lys Gly Leu Asp Tyr Ala
                5               10               15

Ser Gln Gln Gly Thr Ala Ala Leu Gln Lys Glu Leu Lys Arg Ile Lys
            20               25               30

Ile Pro Asp Tyr Ser Asp Ser Phe Lys Ile Lys His Leu Gly Lys Gly
            35               40               45

His Tyr Ser Phe Tyr Ser Met Asp Ile Arg Glu Phe Gln Leu Pro Ser
50               55               60               65

Ser Gln Ile Ser Met Val Pro Asn Val Gly Leu Lys Phe Ser Ile Ser
                70               75               80

Asn Ala Asn Ile Lys Ile Ser Gly Lys Trp Lys Ala Gln Lys Arg Phe
            85               90               95

Leu Lys Met Ser Gly Asn Phe Asp Leu Ser Ile Glu Gly Met Ser Ile
100              105              110

Ser Ala Asp Leu Lys Leu Gly Ser Asn Pro Thr Ser Gly Lys Pro Thr
    115              120              125

Ile Thr Cys Ser Ser Cys Ser Ser His Ile Asn Ser Val His Val His
130              135              140              145

Ile Ser Lys Ser Lys Val Gly Trp Leu Ile Gln Leu Phe His Lys Lys
            150              155              160

Ile Glu Ser Ala Leu Arg Asn Lys Met Asn Ser Gln Val Cys Glu Lys
            165              170              175
```

```
Val Thr Asn Ser Val Ser Ser Lys Leu Gln Pro Tyr Phe Gln Thr Leu
        180             185                 190

Pro Val Met Thr Lys Ile Asp Ser Val Ala Gly Ile Asn Tyr Gly Leu
    195             200             205

Val Ala Pro Pro Ala Thr Thr Ala Glu Thr Leu Asp Val Gln Met Lys
210             215             220             225

Gly Glu Phe Tyr Ser Glu Asn His His Asn Pro Pro Pro Phe Ala Pro
            230             235                 240

Pro Val Met Glu Phe Pro Ala Ala His Asp Arg Met Val Tyr Leu Gly
        245             250             255

Leu Ser Asp Tyr Phe Phe Asn Thr Ala Gly Leu Val Tyr Gln Glu Ala
        260             265             270

Gly Val Leu Lys Met Thr Leu Arg Asp Asp Met Ile Pro Lys Glu Ser
    275             280             285

Lys Phe Arg Leu Thr Thr Lys Phe Phe Gly Thr Phe Leu Pro Glu Val
290             295             300             305

Ala Lys Lys Phe Pro Asn Met Lys Ile Gln Ile His Val Ser Ala Ser
            310             315             320

Thr Pro Pro His Leu Ser Val Gln Pro Thr Gly Leu Thr Phe Tyr Pro
            325             330             335

Ala Val Asp Val Gln Ala Phe Ala Val Leu Pro Asn Ser Ser Leu Ala
            340             345             350

Ser Leu Phe Leu Ile Gly Met His Thr Thr Gly Ser Met Glu Val Ser
    355             360             365

Ala Glu Ser Asn Arg Leu Val Gly Glu Leu Lys Leu Asp Arg Leu Leu
370             375             380             385

Leu Glu Leu Lys His Ser Asn Ile Gly Pro Phe Pro Val Glu Leu Leu
            390             395             400

Gln Asp Ile Met Asn Tyr Ile Val Pro Ile Leu Val Leu Pro Arg Val
            405             410             415

Asn Glu Lys Leu Gln Lys Gly Phe Pro Leu Pro Thr Pro Ala Arg Val
            420             425             430

Gln Leu Tyr Asn Val Val Leu Gln Pro His Gln Asn Phe Leu Leu Phe
    435             440             445

Gly Ala Asp Val Val Tyr Lys
450             455
```

THERAPEUTIC COMPOSITIONS COMPRISING BACTERICIDAL/PERMEABILITY-INCREASING (BPI) PROTEIN PRODUCTS

This is a continuation-in-part of U.S. application Ser. No. 08/530,599 filed Sep. 19, 1995, now abandoned, which is in turn a continuation-in-part of U.S. application Ser. No. 08/372,104 filed Jan. 13, 1995, now abandoned, all of which are incorporated herein by reference.

BACKGROUND OF THE INVENTION

The present invention relates generally to improved therapeutic compositions and treatment methods utilizing poloxamer (polyoxypropylene-polyoxyethylene block copolymer) surfactants for enhancing the activity of bactericidal/permeability-increasing protein (BPI protein products.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 1 hereto. U.S. Pat. No. 5,198,541 discloses recombinant genes encoding and methods for expression of BPI proteins, including BPI holoprotein and fragments of BPI.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., *Infect. Immun.* 60:4754–4761 (1992).

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). BPI is commonly thought to be non-toxic for other microorganisms, including yeast, and for higher eukaryotic cells. Elsbach and Weiss (1992), supra, reported that BPI exhibits anti-bacterial activity towards a broad range of gram-negative bacteria at concentrations as low as $10^{-8}$ to $10^{-9}$M, but that 100- to 1,000-fold higher concentrations of BPI were non-toxic to all of the gram-positive bacterial species, yeasts, and higher eukaryotic cells tested at that time. It was also reported that BPI at a concentration of $10^{-6}$M or 160 μg/ml had no toxic effect, when tested at a pH of either 7.0 or 5.5, on the gram-positive organisms *Staphylococcus aureus* (four strains), *Staphylococcus epidermidis*, *Streptococcus faecalis*, *Bacillus subtilis*, *Micrococcus lysodeikticus*, and *Listeria monocytogenes*. BPI at $10^{-6}$M reportedly had no toxic effect on the fungi *Candida albicans* and *Candida parapsilosis* at pH 7.0 or 5.5, and was non-toxic to higher eukaryotic cells such as human, rabbit and sheep red blood cells and several human tumor cell lines. See also Elsbach and Weiss, *Advances in Inflammation Research*, ed. G. Weissmann, Vol. 2, pages 95–113 Raven Press (1981). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of Mg$^{++}$ and Ca$^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [Weiss et al., *J. Clin. Invest.* 65: 619–628 (1980)]. This first stage of BPI action, permeabilization of the gram-negative outer envelope, is reversible upon dissociation of the BPI, a process requiring the presence of divalent cations and synthesis of new LPS [Weiss et al., *J. Immunol.* 132: 3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et al., *J. Clin. Invest.* 86: 631–641 (1990)). Specific investigation of this possibility has shown that on a molar basis BPI is at least as inhibitory of cytoplasmic membrane vesicle function as polymyxin B (In't Veld et al., *Infection and Immunity* 56: 1203–1208 (1988)) but the exact mechanism as well as the relevance of such vesicles to studies of intact organisms has not yet been elucidated.

BPI is also capable of neutralizing the endotoxic properties of LPS to which it binds. Because of its bactericidal properties for gram-negative organisms and its ability to neutralize LPS, BPI can be utilized for the treatment of mammals suffering from diseases caused by gram-negative bacteria, such as bacteremia or sepsis.

Poloxamer (polyoxypropylene-polyoxyethylene block copolymer) surfactants are non-ionic block copolymer surfactants having a structure composed of two blocks or chains of hydrophilic polyoxyethylene (POE) flanking a single block of hydrophobic polyoxypropylene (POP). They are considered to be among the least toxic of known surfactants and are widely used in foods, drugs and cosmetics.

Of interest to the present invention is co-owned, co-pending allowed U.S. patent application Ser. No. 08/190, 869 (PCT Application Publication No. WO 94/17819), herein incorporated by reference, which describes the improved solubilization or stability of pharmaceutical compositions containing BPI protein products and a poloxamer surfactant, either alone or in combination with a polysorbate surfactant.

Also of interest to the present invention are PCT Application Publication No. WO88/06038 and U.S. Pat. No. 5,183,687, which address use of poloxamer surfactants with and without "conventional" antibiotics in the treatment of viral, Mycobactetium and Coccidioides infections.

There exists a desire in the art for methods and compositions capable of improving the therapeutic effectiveness of antibacterial agents such as BPI protein products. Such methods and compositions could ideally reduce the dosage of agent required to achieve desired therapeutic effects.

SUMMARY OF THE INVENTION

The present invention provides improved anti-microbial compositions and methods of treatment. According to one aspect of the invention, improved therapeutic compositions are provided that comprise a BPI protein product and a polyoxypropylene-polyoxyethylene block copolymer (poloxamer) surfactant that enhances the anti-bacterial activity of the BPI protein product. Presently preferred bactericidal-activity-enhancing poloxamer surfactants include poloxamer 333 (PLURONIC 103, BASF, Parsippany, N.J.), poloxamer 334 (PLURONIC 104, BASF), poloxamer 335 (PLURONIC 105, BASF), or poloxamer 403 (PLURONIC P123, BASF). Poloxamers employed according to the invention may optionally be heat-treated prior to incorporation into the compositions. Especially preferred are compositions including poloxamer 333 or poloxamer 403. This aspect of the invention is based upon the finding that the combination of a BPI protein product with one of the above-listed poloxamer surfactants unexpectedly enhances the bactericidal activity of the BPI protein product, both in vitro and in vivo. The improved therapeutic compositions of the present invention may further comprise ethylenediaminetetraacetic acid (EDTA). This aspect of the invention is based on the discovery that the addition of EDTA to therapeutic compositions containing BPI protein product and a bactericidal-activity-enhancing poloxamer surfactant (such as poloxamer 333, poloxamer 334, poloxamer 335 or poloxamer 403) may produce further enhancement of the bactericidal activity of the BPI protein product.

Corresponding improved methods for treating bacterial infection are also provided, the improvement comprising administering to a patient with a suspected or confirmed infection a therapeutic composition of BPI protein product and a bactericidal-activity-enhancing poloxamer, and optionally EDTA. The present invention also contemplates the use of a bactericidal-activity-enhancing poloxamer surfactant (such as poloxamer 333, poloxamer 334, poloxamer 335, or poloxamer 403) with a BPI protein product, and optionally EDTA, for the manufacture of a medicament for treatment of bacterial infection.

The present invention further provides improved compositions for inhibiting bacterial and fungal growth comprising a BPI protein product and a bacterial and fungal growth-inhibiting enhancing poloxamer surfactant, and optionally EDTA. This aspect of the invention is based upon the discovery that combination of a BPI protein product with a bacterial and fungal growth-inhibiting enhancing poloxamer surfactant unexpectedly enhances the growth-inhibitory activity of the BPI protein product. Corresponding methods of killing or inhibiting the growth of bacteria or fungi are provided that comprise contacting the organisms with a composition comprising a BPI protein product and a bacterial and fungal growth-inhibiting enhancing poloxamer surfactant, and optionally EDTA. Presently preferred bacterial and fungal growth-inhibiting enhancing poloxamer surfactants include poloxamer 333, poloxamer 334, poloxamer 335, and poloxamer 403.

Poloxamers are polyoxypropylene-polyoxyethylene block copolymers that conform generally to the formula: $HO(CH_2CH_2O)_x(CH(CH_3)CH_2O)_y(CH_2CH_2O)_zH$. Poloxamer 333 is a polyoxypropylene-polyoxyethylene block copolymer that conforms generally to the above formula wherein the average values of x, y and z are respectively 20, 54 and 20. Poloxamer 334 is a polyoxypropylene-polyoxyethylene block copolymer that conforms generally to the above formula wherein the average values of x, y and z are respectively 31, 54 and 31. Poloxamer 335 is a polyoxypropylene-polyoxyethylene block copolymer that conforms generally to the above formula wherein the average values of x, y and z are respectively 38, 54 and 38. Poloxamer 403 is a polyoxypropylene-polyoxyethylene block copolymer that conforms generally to the above formula wherein the average values of x, y and z are respectively 21, 67 and 21. *CTFA Cosmetic Ingredient Dictionary*, published by the Cosmetic, Toiletry and Fragrance Association, Washington, D.C. (1991), page 450–451.

With regard to the improved methods for treating bacterial infection described above, a method of improving the therapeutic effectiveness of antibiotics for treatment of bacterial infections is also provided. According to this method, the antibiotic is concurrently administered with a composition comprising a BPI protein product formulated with a BPI-activity-enhancing poloxamer surfactant (such as poloxamer 333, poloxamer 334, poloxamer 335, or poloxamer 403), and optionally with EDTA. This aspect of the invention is based on the discovery that the improvement in therapeutic effectiveness of antibiotics that is seen with the addition of BPI protein product can be further enhanced by various poloxamer formulations, and that the addition of EDTA to the BPI protein product/poloxamer formulation provides an even greater enhancement of the antibiotic's therapeutic effectiveness. This aspect of the invention also provides use of poloxamer surfactants (such as poloxamer 333, poloxamer 334, poloxamer 335, or poloxamer 403), optionally with EDTA, for the manufacture of a medicament containing BPI protein product for co-treatment of a bacterial infection with an antibiotic.

The following findings are illustrative of this aspect of the invention: For a Pseudomonas species, enhancement of the improved therapeutic effectiveness of ceftizoxime was provided by BPI protein product formulations containing poloxamer 333, poloxamer 335, or poloxamer 403; enhancement for ceftriaxone was provided by BPI protein product formulations containing poloxamer 333, poloxamer 335, or poloxamer 403; and enhancement for chloramphenicol was provided by BPI protein product formulations containing poloxamer 333, poloxamer 334, poloxamer 335, or poloxamer 403. For an Acinetobacter species, enhancement for ceftazidime was provided by BPI protein product formulations containing poloxamer 333, poloxamer 334, poloxamer 335, or poloxamer 403; enhancement for ceftriaxone was provided by BPI protein product formulations containing poloxamer 333, poloxamer 334, poloxamer 335, or poloxamer 403; and enhancement for chloramphenicol was provided by BPI protein product formulations containing poloxamer 333, poloxamer 334, poloxamer 335, or poloxamer 403. For a Streptococcus species, enhancement for oxacillin was provided by BPI protein product formulations containing poloxamer 333, poloxamer 334, poloxamer 335, or poloxamer 403. For an Enterococcus species, enhancement for rifampicin was provided by BPI protein product formulations containing poloxamer 335 or poloxamer 403; and enhancement for ciprofloxacin was provided by BPI protein product formulations containing poloxamer 333.

For a Pseudomonas species, enhancement of the therapeutic effectiveness of a variety of antibiotics was provided by a BPI protein product formulation containing poloxamer 403, and even greater enhancement was provided by adding increasing concentrations of EDTA to the BPI/poloxamer 403 formulation.

Numerous additional aspects and advantages of the invention will become apparent to those skilled in the art upon consideration of the following detailed description of the invention which describes presently preferred embodiments thereof.

DETAILED DESCRIPTION

The present invention provides improved anti-microbial compositions and methods of treatment. The improved methods and compositions, in addition to being useful for treatment of bacterial infections and conditions associated therewith or resulting therefrom (such as sepsis and bacteremia), and are also useful for prophylaxis of patients at high risk of bacterial infection, e.g., patients who will undergo abdominal or genitourinary surgery, or trauma victims.

Specifically, the present invention provides, in a therapeutic composition comprising a BPI protein product and a stabilizing poloxamer surfactant, the improvement comprising a bactericidal-activity-enhancing poloxamer surfactant, such as poloxamer 333, poloxamer 334, poloxamer 335, or poloxamer 403. The present invention is based upon the finding that the combination of a BPI protein product with one of these above-listed poloxamer surfactants unexpectedly enhances the bactericidal activity of the BPI protein product, both in vitro and in vivo. The improved therapeutic compositions of the present invention may further comprise EDTA. This aspect of the invention is based on the discovery that the addition of EDTA to some therapeutic compositions containing BPI protein product and a bactericidal-activity-enhancing poloxamer surfactant, such as poloxamer 333, poloxamer 334, poloxamer 335, or poloxamer 403, produces further enhancement of the bactericidal activity of the BPI protein product. Such compositions may optionally comprise pharmaceutically acceptable diluents, adjuvants or carriers. The invention utilizes any of the large variety of BPI protein products known to the art including natural BPI protein, recombinant BPI protein, BPI fragments, BPI analogs, BPI variants, and BPI peptides.

Corresponding improved methods for treating bacterial infection are also provided, the improvement comprising administering to a patient with a suspected or confirmed infection a therapeutic composition of BPI protein product and a bactericidal-activity-enhancing poloxamer, and optionally EDTA. The present invention also contemplates the use of a bactericidal-activity-enhancing poloxamer surfactant (such as poloxamer 333, poloxamer 334, poloxamer 335, or poloxamer 403) with a BPI protein product, and optionally EDTA, for the manufacture of a medicament for treatment of bacterial infection. The therapeutic composition of BPI protein product and poloxamer surfactant with or without EDTA may be administered systemically or topically to a subject suffering from a suspected or confirmed bacterial infection.

Poloxamer 333 is sold by BASF (Parsippany, N.J.) under the name PLURONIC P103 and has a molecular weight of 4950 and a hydrophilic/lipophilic balance (HLB) value of 7–12. Poloxamer 334 is sold by BASF under the name PLURONIC P104 and has a molecular weight of 5900 and an HLB value of 12–18. Poloxamer 335 is sold by BASF under the name PLURONIC P105 and has a molecular weight of 6500 and an HLB value of 12–18. Poloxamer 403 is sold by BASF under the name PLURONIC P123 and has a molecular weight of 5750 and an HLB value of 7–12. Presently preferred bactericidal-activity-enhancing poloxamer surfactants include poloxamer 333, poloxamer 334, poloxamer 335 or poloxamer 403. Especially preferred are compositions including poloxamer 333 or poloxamer 403.

Poloxamers employed according to the invention may optionally be heat-treated prior to incorporation into the compositions. A preferred method of heat treatment is as follows: (1) making a solution of the poloxamer in deionized water, (2) heating the solution to a boil, (3) removing it from heat, (4) allowing it to cool to room temperature, and (5) stiring until the poloxamer is completely solubilized. Alternatively, in the heating step (2), the solution may be boiled for up to 30 minutes or more.

The present invention further provides improved compositions for inhibiting bacterial and fungal growth comprising a BPI protein product and a bacterial and fungal growth-inhibiting enhancing poloxamer surfactant, and optionally EDTA. This aspect of the invention is based upon the discovery that a bacterial and fungal growth-inhibiting enhancing poloxamer surfactant unexpectedly enhances the growth-inhibitory activity of BPI protein product, and that improved compositions comprising such poloxamer surfactants and BPI protein product display superior growth-inhibitory preservative effects. Corresponding methods of killing or inhibiting the growth of bacteria or fungi are provided that comprise contacting the organisms with a composition comprising a BPI protein product and a bacterial and fungal growth-inhibiting enhancing poloxamer surfactant, and optionally EDTA. Presently preferred bacterial and fungal growth-inhibiting enhancing poloxamer surfactants include poloxamer 333, poloxamer 334, poloxamer 335, and poloxamer 403.

These methods can be practiced in vivo or in a variety of in vitro uses such as use as a preservative, use to decontaminate fluids and surfaces, or use to sterilize surgical and other medical equipment and implantable devices, including prosthetic joints. These methods can also be used for in situ sterilization of indwelling invasive devices such as intravenous lines and catheters which are often foci of infection and in the preparation of growth media for cells. The efficacy of the improved compositions for inhibiting bacterial and fungal growth can be evaluated according to the assay described below in Example 8, or by any of the assays described in co-owned, copending patent application Cohen et al., U.S. Ser. No. 08/125,651 filed Sep. 22, 1993, and continuation-in-part thereof U.S. Ser. No. 08/273,401 filed Jul. 11, 1994, and continuation-in-part thereof U.S. Ser. No. 08/311,611 filed Sep. 22, 1994, and corresponding PCT Application No. PCT/US94/11225, and co-owned, copending patent application (Little et al.) U.S. Ser. No. 08/183,222 filed Jan. 14, 1994, and continuation-in-part thereof U.S. Ser. No. 08/209,762 filed Mar. 11, 1994, and continuation-in-part thereof (Horwitz et al.) U.S. Ser. No. 08/274,299 filed Jul. 11, 1994, and continuation-in-part thereof U.S. Ser. No. 08/372,783 filed Jan. 13, 1995, and corresponding PCT Application No. PCT/US95/00656, and co-owned, copending patent application Little et al., U.S. Ser. No. 08/183,222 filed Jan. 14, 1994, and continuation-in-part thereof U.S. Ser. No. 08/209, 762 filed Mar. 11, 1994, and continuation-in-part thereof U.S. Ser. No. 08/273,540 filed Jul. 11, 1994, and continuation-in-part thereof U.S. Ser. No. 08/372,105 filed Jan. 13, 1995, and corresponding PCT Application No. PCT/US95/00498, all of which are incorporated herein by reference.

BPI protein product is thought to interact with a variety of host defense elements present in whole blood or serum, including complement, p15 and LBP, and other cells and components of the immune system. Such interactions may result in potentiation of the activities of BPI protein product. Because of these interactions, BPI protein products can be expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. [Weiss et al., *J. Clin. Invest.* 90:1122–1130 (1992)]. This is also shown in in vivo animal experiments (see, e.g., co-owned, copending U.S. Application Cohen et al., U.S. Ser. No. 08/311,611 filed Sep. 22, 1994, and corresponding PCT Appl. No. PCT/US94/ 11225, all of which are incorporated herein by reference. This may be because conventional in vitro systems lack the blood elements that facilitate or potentiate BPI's function in vivo, or because conventional media contain higher than physiological concentrations of magnesium and calcium, which are typically inhibitors of the anti-bacterial activity of BPI protein products. Furthermore, in the host, BPI protein product is available to neutralize endotoxin released during host infection, including from stress-induced translocation of gram-negative bacteria or from antibiotic treatment of gram-negative bacteria, a further clinical benefit not seen in or predicted by in vitro tests.

It is also contemplated that the BPI protein product be administered with other products that potentiate the bactericidal activity of BPI protein products. For example, serum complement potentiates the gram-negative bactericidal activity of BPI protein products; the combination of BPI protein product and serum complement provides synergistic bactericidal/growth inhibitory effects. See, e.g., Ooi et al. *J. Biol. Chem.*, 265: 15956 (1990) and Levy et al. *J. Biol. Chem.*, 268: 6038–6083 (1993) which address naturally-occurring 15 kD proteins potentiating BPI antibacterial activity. See also co-owned, co-pending PCT Application No. US94/07834 filed Jul. 13, 1994, which corresponds to U.S. patent application Ser. No. 08/274,303 filed Jul. 11, 1994 as a continuation-in-part of U.S. patent application Ser. No. 08/093,201 filed Jul. 14, 1993. These applications, which are all incorporated herein by reference, describe methods for potentiating gram-negative bactericidal activity of BPI protein products by administering lipopolysaccharide binding protein (LBP) and LBP protein products. LBP protein derivatives and derivative hybrids which lack CD-14 immunostimulatory properties are described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are hereby incorporated by reference.

An advantage provided by the present invention is the ability to provide more effective killing or growth inhibition of bacteria and fungi and enhanced anti-bacterial or anti-fungal activity of the BPI protein product.

Therapeutic compositions comprising BPI protein product and a BPI anti-microbial activity enhancing poloxamer surfactant, and optionally containing EDTA, may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), transpulmonary using aerosolized or nebulized drug, or transdermal. For example, when given parenterally, BPI protein product compositions are generally injected in doses ranging from 1 $\mu$g/kg to 100 mg/kg per day, and preferably at doses ranging from 0.1 mg/kg to 20 mg/kg per day. The treatment may continue at the same, reduced or increased dose per day for, e.g., 1 to 3 days, and additionally as determined by the treating physician. Topical routes include administration in the form of salves, ophthalmic drops, ear drops, irrigation fluids (for, e.g., irrigation of wounds) or medicated shampoos. For example, for topical administration in drop form, about 10 to 200 $\mu$L of a BPI protein product composition may be applied one or more times per day as determined by the treating physician. Those skilled in the art can readily optimize effective dosages and administration regimens for therapeutic compositions comprising BPI protein product and a BPI bactericidal-activity enhancing poloxamer surfactant, and optionally containing EDTA, as determined by good medical practice and the clinical condition of the individual patient.

With regard to the improved methods for treating bacterial infection described above, a method of improving the therapeutic effectiveness of antibiotics for treatment of bacterial infections is also provided. According to this method, the antibiotic is concurrently administered with a composition comprising a BPI protein product formulated with a BPI-activity-enhancing poloxamer surfactant (such as poloxamer 333, poloxamer 334, poloxamer 335, or poloxamer 403), and optionally with EDTA. This aspect of the invention is based on the discovery that the improvement in therapeutic effectiveness of antibiotics that is seen with the addition of BPI protein product can be further enhanced by various poloxamer formulations, and that the addition of EDTA to the BPI protein product/poloxamer formulation provides an even greater enhancement of the antibiotic's therapeutic effectiveness. This aspect of the invention also provides use of poloxamer surfactants (such as poloxamer 333, poloxamer 334, poloxamer 335, or poloxamer 403), optionally with EDTA, for the manufacture of a medicament containing BPI protein product for co-treatment of a bacterial infection with an antibiotic.

For this aspect of the invention, the improved therapeutic effectiveness of antibiotics seen upon concurrent administration with BPI protein product can be observed in a number of ways. For example, a BPI protein product may convert an organism that is clinically resistant to an antibiotic into an organism that is clinically susceptible to the antibiotic, or may otherwise improve the antibiotic susceptibility of that organism. The BPI protein product and antibiotic may have a therapeutic effect when both are given in doses below the amounts sufficient for monotherapeutic effectiveness. The inclusion of a BPI-activity-enhancing poloxamer surfactant in the BPI protein product formulation provides a further enhancement of these activities. Co-owned, copending patent application Cohen et al., U.S. Ser. No. 08/125,651 filed Sep. 22, 1993, and continuation-in-part thereof U.S. Ser. No. 08/273,401 filed Jul. 11, 1994, and continuation-in-part thereof U.S. Ser. No. 08/311,611 filed Sep. 22, 1994, and corresponding PCT Application No. PCT/US94/11225, and co-owned, copending patent application (Little et al.), U.S. Ser. No. 08/183,222 filed Jan. 14, 1994, and continuation-in-part thereof U.S. Ser. No. 08/209,762 filed Mar. 11, 1994, and continuation-in-part thereof (Horwitz et al.) U.S. Ser. No. 08/274,299 filed Jul. 11, 1994, and continuation-in-part thereof U.S. Ser. No. 08/372,783 filed Jan. 13, 1995, and corresponding PCT Application No. PCT/US95/00656, all of which are incorporated herein by reference, disclose methods for evaluating the use of BPI as an anti-microbial agent and to enhance the effectiveness of antibiotics.

The improved therapeutic effectiveness of antibiotics may be demonstrated in in vivo animal models, or may be predicted on the basis of a variety of in vitro tests, including (1) determinations of the minimum inhibitory concentration (MIC) of an antibiotic required to inhibit growth of a gram-negative organism for 24 hours, (2) determinations of the effect of an antibiotic on the kinetic growth curve of a gram-negative organism, and (3) checkerboard assays of the MIC of serial dilutions of antibiotic alone or in combination with serial dilutions of BPI protein product. Such improved effectiveness may be demonstrated by (a) a reduction in the number of organisms, (b) a reduced MIC, and/or (c) reversal of the organism's resistance to the antibiotic. Exemplary models or tests are described in Eliopoulos and Moellering In *Antibiotics in Laboratory Medicine*, 3rd ed. (Lorian, V., Ed.) pp. 432–492, Williams and Wilkins, Baltimore Md. (1991).

"Concurrent administration," or co-treatment, as used herein includes administration of the agents, in conjunction or combination, together, or before or after each other. The BPI protein product (formulated with activity-enhancing poloxamer) and antibiotics may be administered by different routes. For example, the formulated BPI protein product may be administered intravenously while the antibiotics are administered intramuscularly, intravenously, subcutaneously, orally or intraperitoneally. Alternatively, the formulated BPI protein product may be administered intraperitoneally while the antibiotics are administered intraperitoneally or intravenously, or the formulated BPI protein product may be administered in an aerosolized or nebulized form while the antibiotics are administered, e.g., intravenously. The formulated BPI protein product and antibiotics are preferably both administered intravenously. The formulated BPI protein product and antibiotics may be given sequentially in the same intravenous line, after an intermediate flush, or may be given in different intravenous lines. The formulated BPI protein product and antibiotics may be administered simultaneously or sequentially, as long as they are given in a manner sufficient to allow both agents to achieve effective concentrations at the site of infection.

Concurrent administration of formulated BPI protein product and antibiotic is expected to provide more effective treatment of bacterial infections. Concurrent administration of the two agents may provide greater therapeutic effects in vivo than either agent provides when administered singly. It may permit a reduction in the dosage of one or both agents with achievement of a similar therapeutic effect. Alternatively, the concurrent administration may produce a more rapid or complete bactericidal/bacteriostatic effect than could be achieved with either agent alone.

Therapeutic effectiveness is correlated with a successful clinical outcome, and does not require that the antimicrobial agent or agents kill 100% of the organisms involved in the infection. Success depends on achieving a level of antibacterial activity at the site of infection that is sufficient to inhibit the bacteria in a manner that tips the balance in favor of the host. When host defenses are maximally effective, the antibacterial effect required may be minimal. Reducing organism load by even one log (a factor of 10) may permit the host's own defenses to control the infection. In addition, augmenting an early bactericidal/bacteriostatic effect can be more important than long-term bactericidal/bacteriostatic effect. These early events are a significant and critical part of therapeutic success, because they allow time for host defense mechanisms to activate. Increasing the bactericidal rate may be particularly important for infections such as meningitis, bone or joint infections [Stratton, *Antibiotics in Laboratory Medicine*, 3rd ed. (Lorian, V., Ed.) pp. 849–879, Williams and Wilkins, Baltimore Md. (1991)], or alternatively, for infections involving slow-growing organisms which may have a decreased sensitivity to antibiotics.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as rBPI$_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, and corresponding PCT Application No. PCT/US95/03125, the disclosures of which are incorporated herein by reference. Preferred dimeric products include dimeric BPI protein products wherein the monomers are amino-terminal BPI fragments having the N-terminal residues from about 1 to 175 or about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Similarly configured hybrid fusion proteins involving part or all Lipopolysaccharide Binding Protein (LBP) are also contemplated for use in the present invention.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132 filed Mar. 11, 1994, and corresponding PCT Application No. PCT/US95/03125, the disclosures of which are incorporated herein by reference.

Other BPI protein products useful according to the methods of the invention are peptides derived from or based on BPI produced by recombinant or synthetic means (BPI-derived peptides), such as those described in co-owned and co-pending U.S. patent application Ser. No. 08/504,841 filed Jul. 20, 1995 and in co-owned and copending PCT Application No. PCT/US94/10427 filed Sep. 15, 1994, which corresponds to U.S. patent application Ser. No. 08/306,473 filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as $rBPI_{23}$ or $rBPI_{21}$, or dimeric forms of these N-terminal fragments (e.g., $rBPI_{42}$ dimer). Additionally, preferred BPI protein products include $rBPI_{50}$ and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. One pharmaceutical composition containing BPI protein products (e.g., $rBPI_{50}$, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another pharmaceutical composition containing BPI protein products (e.g., $rBPI_{21}$) comprises the BPI protein product at a concentration of 2 mg/mL in 5 mM citrate, 150 mM NaCl, 0.2% poloxamer 188 and 0.002% polysorbate 80. Such combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Other aspects and advantages of the present invention will be understood upon consideration of the following illustrative examples. Example 1 addresses the effects of poloxamer 403 or poloxamer 334 on the bactericidal activity of BPI protein products against *S. aureus* or *A. baumannii* (formerly *A. anitratus*) in water. Example 2 addresses the effects of poloxamer 333 or poloxamer 403 on the bactericidal activity of non-formulated or formulated BPI protein products against *A. baumannii, S. aureus, N. meningiditis* or *P. aeruginosa* in serum, broth or water. Example 3 addresses the effects of poloxamer 333 or poloxamer 334 on the bactericidal activity of BPI protein products against *S. pneumoniae, S. aureus, E. faecium*, or *A. baumannii* in water. Example 4 relates to uses of other poloxamers. Example 5 addresses the effects of poloxamers 188, 333, 334, 335, or 403 (with or without EDTA) on the bactericidal activity of BPI protein products against *A. baumannii, S. aureus, S. pneumoniae, E. faecium*, or *P. aeruginosa* in serum, Mueller-Hinton broth, tryptic soy broth, or water. Example 6 addresses the effect of compositions containing BPI protein product and poloxamer 188, 333, 334, 335, or 403 in the presence or absence of EDTA on the susceptibility of a variety of organisms to antibiotics. Example 7 addresses the effect of compositions containing BPI protein product and an anti-bacterial activity-enhancing poloxamer surfactant in a rabbit model of corneal injury and ulceration. Example 8 addresses the effect of compositions containing BPI protein product and poloxamer 188 or 403 in the presence or absence of EDTA on the growth of various bacteria and fungi.

EXAMPLE 1
BACTERICIDAL ACTIVITY OF COMPOSITIONS CONTAINING BPI PROTEIN PRODUCT AND POLOXAMER 403 OR POLOXAMER 334 ON *S. AUREUS* AND *A. BAUMANNII* IN WATER

The bactericidal activity of therapeutic compositions comprising BPI protein product and either poloxamer 403 (PLURONIC P123, BASF Wyandotte Corp., Parsippany, N.J.), heat-treated PLURONIC 123, or heat-treated poloxamer 334 (PLURONIC P104, BASF Wyandotte Corp.), was evaluated against clinical isolates of bacteria from the Microscan® library (Dade Microscan, West Sacramento, Calif.). Therapeutic compositions comprising 1 mg/mL $rBPI_{21}$ and 0.1% (w/v) PLURONIC P123, or heat-treated PLURONIC P123, were formulated by diluting a 2 mg/mL solution of "non-formulated" $rBPI_{21}$ (in buffer comprising 5 mM sodium citrate and 150 mM NaCl, without any surfactants) at a 1:2 ratio with a 0.2% solution of the PLURONIC P123. A therapeutic composition comprising 2 mg/mL $rBPI_{21}$ and 0.1% (w/v) heat-treated PLURONIC P104 was prepared. Poloxamer control solutions containing only 0.1% PLURONIC P123 or 0.1% heat-treated PLURONIC P123, and no $rBPI_{21}$, were also prepared.

Sterile stock solutions of 1.0% PLURONIC P123 were-prepared by stirring the PLURONIC P123 in deionized water until dissolved and filtering the solution through a 0.22 μm Nalgene filter unit (Nalge Co., Rochester, N.Y.). Sterile stock solutions of heat-treated PLURONIC P123 were prepared using the following procedure: (1) making a 1.0% (w/v) solution of PLURONIC P123 in deionized water, (2) heating the solution to a boil, (3) removing it from heat, (4) allowing it to cool to room temperature, (5) stirring until the PLURONIC P123 was completely solubilized, and (6) filtering the solution through a 0.22 μm Nalgene filter unit for sterilization. Alternatively, the stock solutions may be autoclaved for sterilization. Heat-treated PLURONIC P104 was prepared similarly.

The bacteria to be used in the assays, *S. aureus* Microscan® ID no. 052-106) and *A. baumannii* (Microscan® ID no. 12291), were grown on tryptic soy agar (TSA) plates (Remel, Catalog #01-920, Lenexa, Kans.) for 24 hours. A bacterial stock emulsion of about 4 to $7\times10^4$ cells/mL was prepared by emulsifying bacterial colonies in sterile water for injection (Kendall McGaw Laboratory, Irvine, Calif.) to a 0.5 McFarland standard and diluting further by 1:10 in water. Assays were conducted by adding 944 μL of sterile water for injection to 4.5 mL polypropylene tubes (Nalgene Cryovial, Nalge Co., Rochester, N.Y.), followed by 40 μL of the bacterial emulsion, followed by 16 μL of the 1 mg/mL $rBPI_{21}$/0.1% PLURONIC P123 therapeutic composition or poloxamer control solution (or 8 μL of the 2 mg/mL $rBPI_{21}$/0.1% PLURONIC P104 therapeutic composition). The tubes were mixed by inversion and incubated at 37° C. for 30 minutes. Following incubation, the remaining colony forming units (CFU) were counted at a $10^{-2}$ dilution by plating 10 μL from each tube onto TSA plates, and at $10^{-4}$ dilutions by plating a 1:100 dilution of 10 μL from each tube onto TSA plates. The TSA plates were incubated at 37° C. for 18 hours and the number of bacterial colonies were visually counted. Results are shown below in Tables 1 and 2.

TABLE 1

| S. aureus | CFU |
|---|---|
| Positive Control | 150000 |
| 16 μg/mL $rBPI_{21}$ with 0.1% PLURONIC P123 | 26600 |
| 16 μg/mL $rBPI_{21}$ with 0.1% heat-treated PLURONIC P123 | 26400 |
| 0.1% PLURONIC P123 control | 150000 |
| 0.1% heat-treated PLURONIC P123 control | 150000 |
| 16 μg/mL $rBPI_{21}$ with 0.1% heat-treated PLURONIC P104 | 49100 |

TABLE 2

| A. baumannii | CFU |
|---|---|
| Positive Growth Control (no $rBPI_{21}$ and no poloxamer) | 63000 |
| 16 μg/mL $rBPI_{21}$ with 0.1% PLURONIC P123 | <100 |
| 16 ug/mL $rBPI_{21}$ with 0.1% heat-treated PLURONIC P123 | 100 |
| 0.1% PLURONIC P123 control | 70000 |
| 0.1% heat-treated PLURONIC P123 control | 70000 |
| 16 μg/mL $rBPI_{21}$ with 0.1% heat-treated PLURONIC P104 | 100 |

EXAMPLE 2
BACTERICIDAL ACTIVITY OF COMPOSITIONS CONTAINING BPI PROTEIN PRODUCT AND POLOXAMER 333 ON *S. AUREUS* AND *A. BAUMANNII* IN SERUM, BROTH OR WATER

The bactericidal activity of therapeutic compositions comprising BPI protein product and either poloxamer 333 (PLURONIC P103, BASF Wyandotte Corp.) or heat-treated PLURONIC P103, was evaluated against the clinical isolates of Example 1. Therapeutic compositions comprising 160 μg/mL $rBPI_{21}$ and varying concentrations of either PLURONIC P103 or heat-treated PLURONIC P103 were formulated by diluting a 2 mg/mL solution of "non-formulated" $rBPI_{21}$ (in buffer comprising 5 mM sodium citrate and 150 mM NaCl, without any surfactants) with the appropriate amounts of PLURONIC P103 or heat-treated PLURONIC P103 solutions. A "formulated" $rBPI_{21}$ solution containing 2 mg/mL $rBPI_{21}$, 0.2% poloxamer 188 (PLURONIC F68, BASF Wyandotte Corp.), 0.002% TWEEN 80 (polysorbate 80, ICI Americas, Wilmington, Del.), 5 mM sodium citrate and 150 mM NaCl was also tested for comparison. Poloxamer control solutions containing only 0.1% PLURONIC P103 or 0.1% heat-treated PLURONIC P103, and no $rBPI_{21}$, were also prepared.

A 0.1% (w/v) solution of PLURONIC P103 was prepared by stirring the PLURONIC P103 in deionized water until dissolved and filtering the solution through a 0.22 μm cellulose acetate polystyrene filter unit (Corning Inc., Corning, N.Y.). Sterile stock solutions of heat-treated PLURONIC P103 were prepared using the following procedure: (1) making a 0.1% (w/v) solution of PLURONIC P103 in deionized water, (2) boiling the solution for 30 minutes, (3) allowing it to cool to room temperature, (4) stirring until the PLURONIC P103 was completely solubilized, and (5) filtering the solution through a 0.22 μm Acrodisc filter unit (Gelman Sciences, Ann Arbor, Mich.) for sterilization.

The bacteria to be used in the assays were grown on tryptic soy agar (TSA) plates (Remel, Catalog #01-920, Lenexa, Kans.) for 24 hours. The S. aureus were grown for an additional 2 hours in Fildes enriched medium. A bacterial stock emulsion was prepared by emulsifying bacterial colonies in sterile deionized water to approximately 2.2 to $3.8 \times 10^8$ colony forming units (CFU)/mL as measured by a Microscan® Turbidity Meter (Dade Microscan, West Sacramento, Calif.), and diluting further by 1:10 in water. Assays were conducted in 96-well flat-bottom microtiter plates (Corning, catalog #25860-96) by adding to each well: 170 μL of serum (Sigma #S1764, St. Louis, Mo.), tryptic soy broth (TSB, Remel, catalog #08-942, Lenexa, Kans.) or sterile water for injection (Kendall McGaw); 10 μL of the bacterial emulsion (or water, as a control); 20 μL of the indicated 160 μg/mL $rBPI_{21}$/poloxamer therapeutic composition (or the poloxamer control solution or water alone as a control). The final concentrations of bacteria in each well were about 4 to $7 \times 10^5$ CFU/mL. The well contents were mixed and the plates were incubated at 37° C. for 4 hours. Following incubation, the remaining colony forming units (CFU) in each well were counted at a $10^{-2}$ dilution by plating 10 μL from each well onto TSA plates. The TSA plates were incubated at 37° C. for 24 hours and the number of bacterial colonies were visually counted. Results are shown below in Table 3; colony counts for the control wells are shown below in Tables 4 and 5.

TABLE 4

Growth Controls for A. baumannii (in 100's of CFUs)

| | | |
|---|---|---|
| Serum | NF $rBPI_{21}$ (no P103) | >2000 |
| | bacteria only | >2000 |
| | 0.1% heat-treated P103 (no BPI) | >2000* |
| | 0.1% P103 (no BPI) | >2000 |
| Broth | NF $rBPI_{21}$ (no P103) | >5000 |
| | bacteria only | >5000 |
| | 0.1% heat-treated P103 (no BPI) | >5000 |
| | 0.1% P103 (no BPI) | >5000 |
| Water | NF $rBPI_{21}$ | 519 |
| | bacteria only | >2000 |
| | 0.1% heat-treated P103 (no BPI) | >2000 |
| | 0.1% P103 (no BPI) | >2000 |

*Contaminated
NF = non-formulated, i.e., prepared without surfactants

TABLE 5

Growth controls for S. aureus (in 100's of CFUs)

| Serum and S. aureus | Serum and S. aureus and 0.1% heat-treated P103 | Broth and S. aureus | Broth and S. aureus and 0.1% heat-treated P103 | Water and S. aureus | Water and S. aureus and 0.1% heat-treated P103 |
|---|---|---|---|---|---|
| 2260 | 2540 | 2960 | 4240 | 550 | 390 |

Additional experiments were performed to test therapeutic compositions, prepared by diluting a variety of formulated BPI protein products with heat-treated PLURONIC P104 solution, and tested against A. baumannii in serial 2-fold dilutions of serum. In these experiments, it was noted that some bactericidal activity was observed at lower serum concentrations (as evidenced by a serial 50% reduction in

TABLE 3

| Row No. | Contents of well (starting $rBPI_{21}$ solution; type of poloxamer preparation; organism) | 100's of CFU remaining after incubation with serum and 16 μg/mL $rBPI_{21}$ formulated with poloxamer at: | | | | 100's of CFU remaining after incubation with broth and 16 μg/mL $rBPI_{21}$ formulated with poloxamer at: | | | | 100's of CFU remaining after incubation with water and 16 μg/mL $rBPI_{21}$ formulated with poloxamer at: | | | |
|---|---|---|---|---|---|---|---|---|---|---|---|---|---|
| | | 0.1% Formulation Conc. | 0.05% Formulation Conc. | 0.01% Formulation Conc. | 0.005% Formulation Conc. | 0.1% Formulation Conc. | 0.05% Formulation Conc. | 0.01% Formulation Conc. | 0.005% Formulation Conc. | 0.1% Formulation Conc. | 0.05% Formulation Conc. | 0.01% Formulation Conc. | 0.005% Formulation Conc. |
| A | NF $rBPI_{21}$ + heat-treated P103 + A. baumannii | >2000 | >2000 | >2000 | >2000 | 0 | 0 | 0 | 0 | 0 | 0 | 0 | 0 |
| B | NF $rBPI_{21}$ + P103 + A. baumannii | >2000 | >2000 | >2000 | >2000 | 0 | 0 | 0 | 0 | 0 | 0 | 0 | 0 |
| D | F $rBPI_{21}$ + heat-treated P103 + A. baumannii | >2000 | >2000 | >2000 | >2000 | 0 | 0 | * | 0 | 0 | >2000 | 0 | 0 |
| E | F $rBPI_{21}$ + P103 + A. baumannii | >2000 | >2000 | >2000 | >2000 | 0 | 0 | 51 | 252 | 0 | 0 | 0 | 0 |
| G | NF $rBPI_{21}$ + heat-treated P103 + S. aureus | >1000 | >1000 | >1000 | >1000 | >2000 | >2000 | >2000 | >2000 | 0 | 0 | 0 | 0 |

NF = non-formulated, i.e. prepared without surfactants
F = formulated with 0.2% poloxamer 188 and 0.002% polosorbate 80
* = Contaminated CFUs that correlated to the serial 2-fold reduction in serum concentration). For $rBPI_{23}$, bactericidal activity was observed at serum concentrations of 12.5% and lower. For $rBPI_{21}$, bactericidal activity was observed at serum concentrations of 6.25% and lower. For rBPI$_{42}$ dimer and rBPI$_{50}$, bactericidal activity was observed at dilutions of 1.6% and lower.

In other experiments performed in a similar manner with Microscan® Pluronic Inoculum Water (Dade Microscan, West Sacramento, Calif.), this product exhibited bactericidal activity enhancing effect. In preliminary experiments performed in a similar manner with poloxamer 335 (PLURONIC P105, BASF Wyendotte Corp.), this poloxamer was also observed to have some bactericidal activity enhancing effect.

In further experiments, the bactericidal activity of therapeutic compositions comprising BPI protein product and a poloxamer surfactant was evaluated against clinical isolates of *Neisseria meningiditis* (Type C) (Microscan® ID No. 410-001), *Pseudomonas aeruginosa* (strain 12.4.4, provided by S. M. Opal, Brown University, Providence, R.I.; referenced in Ammons et al., *J. Infect. Diseases*, 170:1473–82 (1994)), and *Acinetobacter baumannii* (Microscan® ID No. 12300). The following therapeutic compositions were prepared, comprising 2 mg/mL rBPI$_{21}$; 0.2% of either (a) poloxamer 188 (PLURONIC F68), (b) poloxamer 333 (PLURONIC P103), (c) poloxamer 334 (PLURONIC P104), (d) poloxamer 335 (PLURONIC P105) or (e) poloxamer 403 (PLURONIC P123); 0.002% polysorbate 80 (TWEEN 80); 5 mM sodium citrate; and 150 mM NaCl. Poloxamer control solutions containing only 0.2% PLURONIC P123, P103 or F68, and no rBPI$_{21}$, were also prepared.

The bacteria to be used in these additional assays were grown for approximately 24 hours on tryptic soy agar (TSA) plates (Remel, Catalog #01-920, Lenexa, Kans.) for *P. aeruginosa* or *A. baumannii* and chocolate agar plates (Remel Catalog #01-301, Lenexa, Kans.) for *N. meningiditis*. A bacterial stock emulsion was prepared by emulsifying bacterial colonies in sterile saline (0.9% sodium chloride Irrigation water, Kendall McGaw Laboratory, Irvine, Calif.) to an equivalent of a 0.5 McFarland standard as measured by a Microscan® Turbidity Meter (Dade Microscan, West Sacramento, Calif.), and diluting further by 1:10 in saline. Assays were conducted in a final volume of 1 mL by adding 982 or 974 μL of Mueller-Hinton Broth with 2% Fildes Enrichment (Remel, Catalog #06-1496, Lenexa, Kans.) for *N. meningitidis* or of Mueller-Hinton Broth plus Cations (CSMHB, Remel) for *P. aeruginosa* to 4.5 mL polypropylene tubes (Nalgene Cryovial, Nalge Co., Rochester, N.Y.), followed by 10 μL of the bacterial emulsion (or broth media, as a control); and 8 or 16 μL of the 2 mg/mL rBPI$_{21}$/poloxamer therapeutic composition. The tubes were mixed by vortexing and incubated at 37° C. for 8 hours. Following incubation, the remaining colony forming units (CFU) were counted at varying dilutions ($10^{-2}$ to $10^{-7}$) by plating 10 μl or 100 μl of an appropriate dilution onto chocolate agar or TSA plates. The chocolate agar or TSA plates were incubated at 37° C. (with 5% $CO_2$ for the *N. meningitidis* plates) for approximately 24 hours and the number of bacterial colonies were visually counted. Results are shown below in Tables 6 and 7.

TABLE 6

| *N. meningiditis*[a] | CFU |
|---|---|
| Control | $9.5 \times 10^7$ |
| 0.2% PLURONIC P123 Control[b] | $7.8 \times 10^7$ |
| 16 μg/mL rBPI$_{21}$ with 0.2% PLURONIC P103[b] | $3 \times 10^3$ |
| 32 μg/mL rBPI$_{21}$ with 0.2% PLURONIC P103[b] | $3 \times 10^3$ |

TABLE 6-continued

| *N. meningiditis*[a] | CFU |
|---|---|
| 0.2% PLURONIC F68 Control[b] | $10.1 \times 10^7$ |
| 16 μg/mL rBPI$_{21}$ with 0.2% PLURONIC F68[b] | $4.22 \times 10^6$ |
| 32 μg/mL rBPI$_{21}$ with 0.2% PLURONIC F68[b] | $1.2 \times 10^3$ |

[a]At t = 0, there were $2.02 \times 10^5$ organisms
[b]Also contains 0.002% TWEEN 80 (polysorbate 80)

TABLE 7

| *P. aeruginosa*[a] | CFU |
|---|---|
| Media Control | $6.0 \times 10^7$ |
| 32 μg/ml rBPI$_{21}$ with 0.2% PLURONIC F68 | $1.2 \times 10^8$ |
| 32 μg/ml rBPI$_{21}$ with 0.2% PLURONIC P103 | $<10^{6b}$ |
| 32 μg/ml rBPI$_{21}$ with 0.2% PLURONIC P104 | $3 \times 10^7$ |
| 32 μg/ml rBPI$_{21}$ with 0.2% PLURONIC P105 | $<10^{6b}$ |
| 32 μg/ml rBPI$_{21}$ with 0.2% PLURONIC P123 | $<10^{6b}$ |

| *A. baumannii*[c] | CFU |
|---|---|
| Media Control | $1.06 \times 10^7$ |
| 16 μg/ml rBPI$_{21}$ with 0.2% PLURONIC F68 | $2.43 \times 10^7$ |
| 16 μg/ml rBPI$_{21}$ with 0.2% PLURONIC P103 | $<10^d$ |
| 16 μg/ml rBPI$_{21}$ with 0.2% PLURONIC P104 | $<10^d$ |
| 16 μg/ml rBPI$_{21}$ with 0.2% PLURONIC P105 | $<10^d$ |
| 16 μg/ml rBPI$_{21}$ with 0.2% PLURONIC P123 | $2.7 \times 10^2$ |

[a]At t = 0, there were $6.4 \times 10^5$ CFUs
[b]No CFUs at tested dilutions of $10^{-6}$ and $10^{-7}$
[c]At t = 0, there were $4.7 \times 10^4$ CFUs
[d]No CFUs at tested dilutions of $10^{-1}$ and $10^{-2}$ EXAMPLE 3
BACTERICIDAL ACTIVITY OF COMPOSITIONS CONTAINING BPI PROTEIN PRODUCT AND POLOXAMER 333 OR POLOXAMER 334 ON A VARIETY OF BACTERIA IN WATER The bactericidal activity of therapeutic compositions comprising BPI protein product and heat-treated PLURONIC P103 or heat-treated PLURONIC P104, was evaluated against the *S. aureus* and *A. baumannii* clinical isolates of Example 1 and the additional organisms *S. pneumoniae* (Microscan® ID no. 145) and *E. faeciun* (Microscan® ID no. 15773). Therapeutic compositions comprising 500 μg/mL rBPI$^{21}$ in a 0.075% (w/v) concentration of either heat-treated PLURONIC P103 or heat-treated PLURONIC P104 were formulated by diluting a 2 mg/mL solution of "non-formulated" rBPI$_2$, or "formulated" rBPI$_2$, with the appropriate amounts of 0.1% heat-treated PLURONIC P103 or heat-treated PLURONIC P104 solutions. Compositions comprising 500 μg/mL non-formulated rBPI$_{21}$ in water alone (without any poloxamers) and poloxamer control solutions containing only 0.1% heat-treated P103 or heat-treated P104 (and no rBPI$_{21}$) were also prepared. A "formulated" rBPI$_{23}$ therapeutic composition containing 1 mg/mL rBPI$_{23}$, 0.1% PLURONIC F68 and 0.002% TWEEN 80 was also tested for comparison.

Sterile stock solutions of heat-treated PLURONIC P103 or heat-treated PLURONIC P104 were prepared using the following procedure: (1) making a 0.1% (w/v) solution of the poloxamer in deionized water, (2) heating the solution to a boil, (3) allowing it to cool to room temperature, (4) stirring until the PLURONIC P103 was completely solubilized, and (5) filtering the solution through a 0.22 μm Nalgene filter for sterilization.

The *S. aureus*, *E. faecium* and *A. baumannii* bacteria were grown on TSA plates (Remel, Catalog #01-920, Lenexa, Kans.), and the *S. pneumoniae* were grown on 5% sheep blood agar plates (Remel, Catalog #01-200, Lenexa, Kans.) for 24 hours. A bacterial stock emulsion was prepared by emulsifying bacterial colonies in sterile deionized water to approximately 2.2 to 3.8×10⁸ CFU/mL as measured by a Microscan® Turbidity Meter, and diluting further by 1:10 in water. Assays for rBPI$_{21}$ therapeutic compositions were conducted in 96-well flat-bottom microtiter plates (Corning, catalog#25860-96) by adding to each well: 185 μL of TSB (Remel, catalog #08-942, Lenexa, Kans.) or sterile water for injection (Kendall McGaw); 8 μL of the bacterial emulsion; 6.3 μL of the indicated 500 μg/mL rBPI$_{21}$/poloxamer therapeutic composition (or poloxamer control solution or water alone). The final concentrations of bacteria in each well were about 4 to 7×10⁵ CFU/mL. Assays for the rBPI$_{23}$ therapeutic composition were conducted in the same way, except 178 μL of broth or water and 13 μL of the 500 μg/mL rBPI$_{23}$ composition were added. The well contents were mixed and the plates were incubated at 37° C. The CFUs in each well were counted at 10⁻² and 10⁻⁴ dilutions after 30 minutes and 3 hours of incubation. Results at 30 minutes and 3 hours, respectively, are shown below in Tables 8 and 9.

In a preliminary experiment using therapeutic compositions containing rBPI$_{21}$ and heat-treated PLURONIC P104, it was noted that adding the therapeutic composition immediately after the diluent (e.g. water), before addition of the bacteria, provided greater enhancement of the bactericidal activity of rBPI$_{21}$ compared to adding the same therapeutic composition after adding bacteria. In another preliminary experiment performed using the same gram-positive and gram-negative organisms, with therapeutic compositions prepared by diluting non-formulated rBPI$_{21}$ with PLURONIC P103 and PLURONIC P104 solutions, no bactericidal activity was observed against the gram-positive organisms in broth at concentrations of up to 64 μg/mL of the rBPI$_{21}$ therapeutic compositions.

TABLE 8

Incubation for 30 minutes

| | | | NF rBPI$_{21}$ alone | NF rBPI$_{21}$ with 0.075% heat-treated P103 | NF rBPI$_{21}$ with 0.075% heat-treated P104 | F rBPI$_{21}$ alone | Control | F rBPI$_{23}$ alone | F rBPI$_{21}$ with 0.075% heat-treated P103 | F rBPI$_{23}$ with 0.075% heat-treated P104 | Control |
|---|---|---|---|---|---|---|---|---|---|---|---|
| S. pneumoniae | water | 100 CFUs | 61 | 47 | 58 | 57 | 75 | 66 | 58 | 43 | 47 |
| | water | 10000 CFUs | 0 | 0 | 1 | 0 | 1 | 1 | 1 | 0 | 0 |
| | broth | 100 CFUs | 290 | 305 | 224 | 355 | 389 | 337 | 340 | 350 | 350 |
| | broth | 10000 CFUs | 4 | 3 | 0 | 4 | 4 | 4 | 5 | 7 | 1 |
| S. aureus | water | 100 CFUs | 315 | 227 | 305 | TNTC | TNTC | TNTC | 220 | 398 | TNTC |
| | water | 10000 CFUs | 2 | 1 | 5 | 36 | 54 | 18 | 3 | 1 | 63 |
| | broth | 100 CFUs | TNTC | TNTC | TNTC | TNTC | TNTC | TNTC | TNTC | TNTC | TNTC |
| | broth | 10000 CFUs | 57 | 68 | 49 | 75 | 65 | 60 | 54 | 75 | 59 |
| E. faecium | water | 100 CFUs | 50 | 33 | 122 | 396 | TNTC | TNTC | 180 | 165 | TNTC |
| | water | 10000 CFUs | 1 | 0 | 3 | 7 | 37 | 15 | 3 | 4 | 35 |
| | broth | 100 CFUs | TNTC | TNTC | TNTC | TNTC | TNTC | TNTC | TNTC | TNTC | TNTC |
| | broth | 10000 CFUs | 89 | 28 | 50 | 55 | 68 | 57 | 51 | 39 | 38 |
| A. anitratus | water | 100 CFUs | 73 | 0 | 1 | 49 | TNTC | 203 | 0 | 0 | TNTC |
| | water | 10000 CFUs | 0 | 0 | 0 | 1 | 16 | 3 | 0 | 0 | 17 |
| | broth | 100 CFUs | TNTC | 68 | 634 | TNTC | TNTC | TNTC | 33 | 67 | TNTC |
| | broth | 10000 CFUs | 24 | 2 | 6 | 28 | 44 | 29 | 0 | 3 | 41 |

TABLE 9

Incubation for 3 minutes

| | | | NF rBPI$_{21}$ alone | NF rBPI$_{21}$ with 0.075% heat-treated P103 | NF rBPI$_{21}$ with 0.075% heat-treated P104 | F rBPI$_{21}$ alone | Control | F rBPI$_{23}$ alone | F rBPI$_{21}$ with 0.075% heat-treated P103 | F rBPI$_{23}$ with 0.075% heat-treated P104 |
|---|---|---|---|---|---|---|---|---|---|---|
| S. pneumoniae | water | 100 CFUs | 0 | 0 | 0 | 0 | 0 | 0 | 0 | 0 |
| | water | 10000 CFUs | | | | | 0 | | | |

TABLE 9-continued

Incubation for 3 minutes

| | | | NF rBPI$_{21}$ alone | NF rBPI$_{21}$ with 0.075% heat-treated P103 | NF rBPI$_{21}$ with 0.075% heat-treated P104 | F rBPI$_{21}$ alone | Control | F rBPI$_{23}$ alone | F rBPI$_{21}$ with 0.075% heat-treated P103 | F rBPI$_{23}$ with 0.075% heat-treated P104 |
|---|---|---|---|---|---|---|---|---|---|---|
| | broth | 100 CFUs | 447 | 377 | 393 | 400 | 337 | 360 | 274 | 400 |
| | broth | 10000 CFUs | | | | | 0 | | | |
| S. aureus | water | 100 CFUs | 12 | 2 | 5 | 340 | TNTC | 840 | 10 | 14 |
| | water | 10000 CFUs | | | | | 36 | | | |
| | broth | 100 CFUs | TNTC | TNTC | TNTC | TNTC | TNTC | TNTC | TNTC | TNTC |
| | broth | 10000 CFUs | | | | | 144 | | | |
| E. faecium | water | 100 CFUs | 1 | 1 | 3 | 28 | TNTC | 498 | 8 | 7 |
| | water | 10000 CFUs | | | | | 36 | | | |
| | broth | 100 CFUs | TNTC | TNTC | TNTC | TNTC | TNTC | TNTC | TNTC | TNTC |
| | broth | 10000 CFUs | | | | | 167 | | | |
| A. baumannii | water | 100 CFUs | 0 | 0 | 0 | 0 | TNTC | 0 | 0 | 0 |
| | water | 10000 CFUs | | | | | 15 | | | |
| | broth | 100 CFUs | 58 | 0 | 0 | 27 | TNTC | 15 | 0 | 0 |
| | broth | 10000 CFUs | | | | | 263 | | | |

EXAMPLE 4
BACTERICIDAL ACTIVITY OF COMPOSITIONS CONTAINING BPI PROTEIN PRODUCT AND OTHER POLOXAMER SURFACTANTS

Therapeutic compositions comprising BPI protein product and other poloxamer surfactants, including poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, or poloxamer 407 [see, e.g., *CTFA International Cosmetic Ingredient Dictionary*, Cosmetic, Toiletry and Fragrance Association, Inc., Washington, D.C. (1991)], especially at pages 447–451] are prepared and tested for capacity to enhance bactericidal activity of BPI protein products as described above in Examples 1, 2 and 3.

EXAMPLE 5
BACTERICIDAL ACTIVITY OF COMPOSITIONS CONTAINING BPI PROTEIN PRODUCT FORMULATED WITH POLOXAMER, WITH OR WITHOUT EDTA, IN SERUM, MUELLER-HINTON BROTH, TRYPTIC SOY BROTH, OR WATER

The bactericidal activity of therapeutic compositions comprising BPI protein product and PLURONIC F68, P103, P104, P105 or P123 were evaluated against the *S. aureus* and *A. baumannii* organisms of Example 1, the *S. pneumoniae* organism of Example 3, an *E. faecium* organism (Microscan® ID No. 16866), and a strain of *P. aeruginosa* from the American Type Culture Collection (ATCC No. 19660). Therapeutic compositions were formulated by adding the appropriate amount of poloxamer to a stock solution of 2.2 mg/mL rBPI$_{21}$ (5 mM sodium citrate, 150 mM NaCl, without poloxamer), to achieve the desired 0.2% (w/v) poloxamer concentration, followed by sterile filtration. Formulated product was stored at 2–8° C. for up to 6 months. Sterile stock solutions of poloxamer were made by dissolving the poloxamer paste in water for injection (WFI, Kendall-McGaw) with mixing to a 1–5% concentration (w/v) at room temperature, followed by sterile filtration. Assays were conducted in 96-well microtiter plates using WFI, tryptic soy broth (TSB, Remel, Lenexa, Kans.), Mueller-Hinton Broth plus Cations (CSMHB, Remel), or 40% pooled human serum in CSMHB (Sigma, St. Louis, Mo.) as growth media, according to the general procedure described above in Examples 2 and 3. The results (in colony forming units after 24 hours of incubation) are displayed below in Table 10, and confirm that the poloxamers can enhance the bactericidal activity of BPI protein product.

TABLE 10

| Organism | Medium | Control | rBPI$_{21}$ only | rBPI$_{21}$ with F68 | rBPI$_{21}$ with P103 | rBPI$_{21}$ with P104 | rBPI$_{21}$ with P105 | rBPI$_{21}$ with P123 |
|---|---|---|---|---|---|---|---|---|
| A. baumannii | Water | $2 \times 10^6$ | <100 | <100 | <100 | <100 | <100 | <100 |
| | TSB | $3 \times 10^6$ | $6 \times 10^2$ | $3 \times 10^2$ | <100 | <100 | <100 | <100 |
| | CSMHB | $2 \times 10^6$ | NT | NT | <100 | 100 | <100 | 300 |
| | Serum | $2 \times 10^5$ | $2 \times 10^5$ | $2 \times 10^5$ | $2 \times 10^5$ | $2 \times 10^3$ | $2 \times 10^5$ | $3 \times 10^3$ |
| S. aureus | Water | $8.2 \times 10^5$ | $3.2 \times 10^4$ | $3.6 \times 10^5$ | $2.3 \times 10^4$ | $3.0 \times 10^4$ | NT | $2.7 \times 10^4$ |
| | TSB | $5.4 \times 10^5$ | $5.7 \times 10^5$ | $7.5 \times 10^5$ | $6.0 \times 10^5$ | $7.2 \times 10^5$ | NT | NT |
| | CSMHB | NT | NT | NT | NT | NT | NT | NT |
| | Serum | $4.2 \times 10^5$ | >1 × 10$^5$ | >1 × 10$^5$ | >1 × 10$^5$ | NT | NT | NT |
| S. pneumoniae | Water | $3.2 \times 10^5$ | NT | >1 × 10$^5$ | <100 | <100 | 400 | <100 |
| | TSB | $3 \times 10^5$ | $5 \times 10^4$ | $4 \times 10^4$ | <100 | $5 \times 10^4$ | $3 \times 10^3$ | <100 |
| | CSMHB | $1 \times 10^7$ | NT | NT | $2 \times 10^3$ | $9 \times 10^2$ | $3 \times 10^4$ | $8 \times 10^3$ |
| | Serum | $3 \times 10^5$ | NT | $2.9 \times 10^5$ | $6 \times 10^4$ | $6 \times 10^4$ | $6 \times 10^4$ | $6 \times 10^4$ |
| E. faecium | Water | $4 \times 10^5$ | 100 | $3 \times 10^3$ | 100 | 300 | 300 | <100 |
| | TSB | $5 \times 10^5$ | $5 \times 10^5$ | $5 \times 10^5$ | $4 \times 10^3$ | $3.1 \times 10^5$ | $6 \times 10^4$ | $1 \times 10^3$ |
| | CSMHB | $1 \times 10^7$ | NT | NT | $8 \times 10^4$ | $4 \times 10^5$ | $2 \times 10^5$ | $6 \times 10^5$ |
| | Serum | $1 \times 10^8$ | NT | NT | $5 \times 10^7$ | $7 \times 10^7$ | $5 \times 10^7$ | $1 \times 10^8$ |
| P. aeruginosa | Water | $1 \times 10^7$ | NT | NT | $3 \times 10^3$ | $2 \times 10^3$ | $7 \times 10^4$ | $2 \times 10^3$ |
| | TSB | NT | NT | NT | NT | NT | NT | NT |
| | CSMHB | $1 \times 10^8$ | NT | $4 \times 10^7$ | $1 \times 10^7$ | $5 \times 10^7$ | $3 \times 10^7$ | $5 \times 10^7$ |
| | Serum | $4 \times 10^7$ | NT | $3 \times 10^7$ | $3 \times 10^6$ | $2 \times 10^7$ | $3 \times 10^7$ | $2 \times 10^7$ |

In additional experiments, the bactericidal activity of therapeutic compositions comprising BPI protein product with a poloxamer surfactant and further comprising varying concentrations of EDTA were evaluated against P. aeruginosa (ATCC 19660). Therapeutic compositions were formulated as described above to achieve the desired concentrations of poloxamer and rBPI$_{21}$ in a buffer of 5 mM sodium citrate, 150 mM NaCl and 0.002% polysorbate 80. Assays were conducted generally as described in Example 2 above for P. aeruginosa and A. baumannii. Results in colony forming units after approximately 24 hours of incubation are displayed below in Table 11, and show that the addition of EDTA can further enhance the bactericidal activity of BPI protein product formulated with PLURONIC P123.

TABLE 11

| P. aeruginosa (ATCC No. 19660)[a] | CFU after incubation | | |
|---|---|---|---|
| | 2 hours incubation | 4 hours incubation | 6 hours incubation |
| Media Control (Mueller-Hinton plus cations) | $4.2 \times 10^3$ | $1 \times 10^5$ | $2.1 \times 10^6$ |
| Placebo Control (Media with formulation buffer and 0.05% EDTA) | $1.3 \times 10^3$ | $1.03 \times 10^5$ | $5.4 \times 10^6$ |
| 16 μg/mL rBPI$_{21}$ with 0.2% PLURONIC P123 without EDTA | $7.0 \times 10^3$ $8.5 \times 10^3$ | $4.5 \times 10^4$ $8.0 \times 10^4$ | $5.4 \times 10^5$ $3.3 \times 10^5$ |
| 16 μg/mL rBPI$_{21}$ with 0.2% PLURONIC P123 + 0.05% EDTA[b] | $6.6 \times 10^3$ | $1.34 \times 10^5$ | $3.3 \times 10^5$ |
| 128 μg/mL rBPI$_{21}$ with 0.2% PLURONIC P123 without EDTA | $5.0 \times 10^3$ | $3 \times 10^4$ | $1 \times 10^5$ |
| 128 μg/mL rBPI$_{21}$ with 0.2% PLURONIC P123 + 0.05% EDTA | $1.7 \times 10^3$ | $3 \times 10^3$ | $5 \times 10^2$ |

[a]At t = 0, there were 4.5 × 10$^3$ organisms.
[b]Also contains 0.002% TWEEN 80 (polysorbate 80).

EXAMPLE 6
EFFECT OF COMPOSITIONS CONTAINING BPI PROTEIN PRODUCT AND POLOXAMER IN THE PRESENCE OR ABSENCE OF EDTA ON THE SUSCEPTIBILITY OF VARIOUS ORGANISMS TO ANTIBIOTICS

The effect of therapeutic compositions of rBPI$_{21}$ formulated with poloxamer, with or without EDTA, was evaluated on the antibiotic susceptibility of the multiple drug resistant A. baumannii, S. pneumoniae, E. faecium and P. aeruginosa organisms of Example 5. Therapeutic compositions were prepared containing 2 mg/mL rBPI$_{21}$ (5 mM sodium citrate, 150 mM NaCl) with a 0.2% (w/v) concentration of PLURONIC F68, P103, P104, P105 or P123. The effect on the antibiotic susceptibility of the organisms was determined in Mueller-Hinton Broth plus Cations (CSMHB, Remel), or 40% pooled human serum in CSMHB (Sigma, St. Louis, Mo.), as follows.

Isolated colonies of the organism from overnight cultures were suspended in Microscan® Inoculum Water to a concentration equivalent to a 0.5 McFarland Standard (approximately 1×10$^8$ CFU/ml), determined using a Microscan® turbidimeter. Aliquots were transferred to either CSMHB or 40% pooled human serum in CSMHB. Each tube contained either a final concentration of 16 μg/mL rBPI$_{21}$ or an equivalent volume of control buffer. Minimal inhibitory concentrations (MIC) for each antibiotic tested, i.e. the lowest concentration of antibiotic which inhibits visible growth, were determined using gram-negative (MB and MC) and gram-positive (MA) Sensititre Trays (Radiometer America, Westlake, Ohio), which allow for the rapid and simultaneous survey of a broad spectrum of standard antibiotics. Any other antimicrobial panel systems known in the art, such as the Microscan® (Dade Microscan, Sacramento, Calif.), Pasco (DIFCO, Detroit, Mich.) and Alamar (Alamar, Sacramento, Calif.) systems, may alternatively be used to assay for antibiotic susceptibility.

Tables 12–15 below display a summary of the results of the antibiotic screening panels, reported for each strain tested as the MIC of the tested antibiotics in the presence of the indicated rBPI$_{21}$ therapeutic composition. The antibiotic susceptibility standards (interpretation of an MIC as clinically resistant (R), intermediate (I) or susceptible (S) according to NCCLS standards) applicable to the organism tested appear in superscript next to the MIC. These results indicate that the improvement in therapeutic effectiveness of antibiotics that is seen with the addition of BPI protein product can be further enhanced by various poloxamer formulations.

TABLE 12

Effect of BPI protein product formulation on antibiotic susceptibility of *P. aeruginosa*

| | | Minimum Inhibitory Concentration (μg/mL) | | | | | |
|---|---|---|---|---|---|---|---|
| Antibiotic Tested | Medium Used | Control (no BPI) | rBPI$_{21}$ with F68 | rBPI$_{21}$ with P103 | rBPI$_{21}$ with P104 | rBPI$_{21}$ with P105 | rBPI$_{21}$ with P123 |
| Ceftizoxime | CSMHB | >128$^R$ | 32$^I$ | 16$^I$ | 128$^R$ | 32$^I$ | 128$^R$ |
| | Serum | 128$^R$ | >128$^R$ | 16$^I$ | 128$^R$ | 16$^I$ | 16$^I$ |
| Ceftriaxone | CSMHB | >128$^R$ | 32$^I$ | 8$^S$ | 128$^R$ | 32$^I$ | 128$^R$ |
| | Serum | 128$^R$ | >128$^R$ | 16$^I$ | 128$^R$ | 16$^I$ | 32$^I$ |
| Chloramphenicol | CSMHB | >32$^R$ | >32$^R$ | 16$^I$ | >32$^R$ | 16$^I$ | 16$^I$ |
| | Serum | >32$^R$ | >32$^R$ | 16$^I$ | 16$^I$ | 16$^I$ | 16$^I$ |

TABLE 13

Effect of BPI protein product formulation on antibiotic susceptibility of *A. baumannii*

| | | Minimum Inhibitory Concentration (μg/mL) | | | | | |
|---|---|---|---|---|---|---|---|
| Antibiotic Tested | Medium Used | Control (no BPI) | rBPI$_{21}$ with F68 | rBPI$_{21}$ with P103 | rBPI$_{21}$ with P104 | rBPI$_{21}$ with P105 | rBPI$_{21}$ with P123 |
| Ceftazidime | CSMHB | 16$^I$ | 32$^R$ | <4$^S$ | <4$^S$ | <4$^S$ | <4$^S$ |
| | Serum | >32$^R$ | 32$^R$ | 16$^I$ | 16$^I$ | 16$^I$ | 16$^I$ |
| Ceftriaxone | CSMHB | 128$^R$ | >128$^R$ | <1$^S$ | <1$^S$ | <1$^S$ | 4$^S$ |
| | Serum | >128$^R$ | >128$^R$ | >128$^R$ | >128$^R$ | >128$^R$ | >128$^R$ |
| Chloramphenicol | CSMHB | >4$^R$ | 1$^S$ | <0.5$^S$ | 1$^S$ | <0.5$^S$ | <0.5$^S$ |
| | Serum | >4$^R$ | >4$^R$ | 2$^S$ | 4$^R$ | >4$^R$ | >4$^R$ |

TABLE 14

Effect of BPI protein product formulation on antibiotic susceptibility of *S. pneumoniae*

| | | Minimum Inhibitory Concentration (μg/mL) | | | | | |
|---|---|---|---|---|---|---|---|
| Antibiotic Tested | Medium Used | Control (no BPI) | rBPI$_{21}$ with F68 | rBPI$_{21}$ with P103 | rBPI$_{21}$ with P104 | rBPI$_{21}$ with P105 | rBPI$_{21}$ with P123 |
| Oxacillin | CSMHB | 32$^R$ | 32$^R$ | <0.25$^S$ | 0.5$^S$ | 1$^S$ | 0.5$^S$ |
| | Serum | 32$^R$ | >32$^R$ | 32$^R$ | 32$^R$ | 32$^R$ | 32$^R$ |

TABLE 15

Effect of BPI protein product formulation on antibiotic susceptibility of *E. faecium*

| | | Minimum Inhibitory Concentration (μg/mL) | | | | | |
|---|---|---|---|---|---|---|---|
| Antibiotic Tested | Medium Used | Control (no BPI) | rBPI$_{21}$ with F68 | rBPI$_{21}$ with P103 | rBPI$_{21}$ with P104 | rBPI$_{21}$ with P105 | rBPI$_{21}$ with P123 |
| Rifampicin | CSMHB | 4$^R$ | 0.5$^S$ | 0.5$^S$ | 0.5$^S$ | 0.5$^S$ | 0.5$^S$ |
| | Serum | 4$^R$ | 1$^S$ | 1$^S$ | >4$^R$ | 0.5$^S$ | 0.5$^S$ |
| Chloramphenicol | CSMHB | 16$^I$ | <4S | <4$^S$ | <4$^S$ | <4$^S$ | <4$^S$ |
| | Serum | 8$^S$ | 8$^S$ | 8$^S$ | 8$^S$ | 8$^2$ | 8$^S$ |
| Ciprofloxacin | CSMHB | 2$^I$ | 1$^S$ | <0.5$^S$ | 1$^S$ | 1$^S$ | 1$^S$ |
| | Serum | 2$^I$ | 1$^S$ | 2$^I$ | 2$^I$ | 2$^I$ | 2$^I$ |

In additional experiments, a BPI protein product, rBPI$_{21}$, was formulated with an anti-bacterial activity enhancing poloxamer, specifically PLURONIC P123, and with various concentrations of EDTA, and was evaluated for its effect on the antibiotic susceptibility of a *Pseudomonas aeruginosa* (ATCC 19660). Antibiotic susceptibility was determined using Microscan® panel plates (Dade Microscan, West Sacramento, Calif.) that allow simultaneous determination of minimum inhibitory concentrations for a number of different antibiotics.

The antimicrobial susceptibility tests performed on the Microscan® panel plates are miniaturizations of the broth dilution susceptibility test. Antimicrobial agents are serially diluted in Mueller-Hinton broth (supplemented with calcium and magnesium, or with sodium chloride for oxacillin, or with thymidine phosphorylase for trimethoprim, sulfamethoxazole and trimethoprim/sulfamethoxazole) to concentrations bridging the range of clinical interest. One well on the 96-well Microscan® plate is a growth control well that contains dehydrated broth only. The remaining wells contain dehydrated broth and antibiotic (or broth and biochemical reagent indicator), which is rehydrated to the desired concentration by inoculation of a standardized suspension of test organism. The chromogenic biochemical agent indicators are used to identify and characterize the species of bacteria based on detection of pH changes and substrate utilization. After incubation overnight, the minimum inhibitory concentration (MIC) of an antibiotic for the test organism is determined by observing the well with the lowest concentration of the antibiotic that shows inhibition of growth. Gram-negative and gram positive organisms may be tested using any of the Microscan® panel plates (Microscan®, Dade Microscan, West Sacramento, Calif.). In these experiments with *P. aeruginosa*, the MIC Plus Type 2 panel plates were used. The concentrations of antibiotics tested in this panel plate are shown below in Table 16. The antibiotic susceptibility standards (interpretation of an MIC as resistant, intermediate or susceptible according to Microscan®'s NCCLS-derived standards) applicable to the gram-negative organisms that may be tested in each panel plate appear below in Table 16A.

TABLE 16

ANTIBIOTIC CONCENTRATIONS TESTED IN MIC PLUS TYPE 2 PANEL PLATE

| Antibiotic | Two-Fold Serial Dilutions Tested ($\mu$g/ml) |
|---|---|
| Amoxicillin/K Clavulanate | 1/0.5–32/16 |
| Ampicillin/Sulbactam | 1/0.5–32/16 |
| Azlocillin | 64 |
| Aztreonam | 1–32 |
| Carbenicillin | 16–128 |
| Cefamandole | 4–32 |
| Cefonicid | 2–16 |
| Cefoperazone | 4–32 |
| Cefotaxime | 2–64 |
| Cefotetan | 4–32 |
| Ceftazidime | 1–32 |
| Ceftizoxime | 2–32 |
| Ceftriaxone | 2–64 |
| Chloramphenicol | 2–16 |
| Ciprofloxacin | 0.25–4 |
| Imipenem | 0.5–16 |
| Mezlocillin | 16–128 |
| Netilmicin | 2–16 |
| Ticarcillin | 16–128 |
| Ticarcillin/K Clavulanate | 16–128 |

TABLE 16A

MICROSCAN MIC PLUS TYPE 2 ANTIBIOTIC SUSCEPTIBILITY RANGES FOR GRAM-NEGATIVE BACTERIA

| | MIC ($\mu$g/ml) | | |
|---|---|---|---|
| Antibiotic | Resistant | Intermediate | Susceptible |
| Amoxicillin/K Clavulanate | $\geq$32/16 | 16/8 | $\leq$8/4 |
| Ampicillin/Sulbactam | $\geq$32/16 | 16/8 | $\leq$8/4 |
| Azlocillin[P] | >64 | | $\leq$64 |
| Aztreonam | $\geq$32 | 16 | $\leq$8 |
| Carbenicillin[E] | $\geq$64 | 32 | $\leq$16 |
| Carbenicillin[P] | >128 | | $\leq$128 |
| Cefamandole | $\geq$32 | 16 | $\leq$8 |
| Cefonicid | >16 | 16 | $\leq$8 |
| Cefoperazone | >32 | 32 | $\leq$16 |
| Cefotaxime | $\geq$64 | 16–32 | $\leq$8 |
| Cefotetan | >32 | 32 | $\leq$16 |
| Ceftazidime | $\geq$32 | 16 | $\leq$8 |
| Ceftizoxime | >32 | 16–32 | $\leq$8 |
| Ceftriaxone | $\geq$64 | 16–32 | $\leq$8 |
| Chloramphenicol | >16 | 16 | $\leq$8 |
| Ciprofloxacin | $\geq$4 | 2 | $\leq$1 |
| Imipenem | $\geq$16 | 8 | $\leq$4 |
| Mezlocillin[E] | $\geq$128 | 32–64 | $\leq$16 |

TABLE 16A-continued

MICROSCAN MIC PLUS TYPE 2 ANTIBIOTIC SUSCEPTIBILITY RANGES FOR GRAM-NEGATIVE BACTERIA

| | MIC ($\mu$g/ml) | | |
|---|---|---|---|
| Antibiotic | Resistant | Intermediate | Susceptible |
| Mezlocillin[P] | $\geq$128 | | $\leq$64 |
| Netilmicin | >16 | 16 | $\leq$8 |
| Ticarcillin[E] | $\geq$128 | 32–64 | $\leq$16 |
| Ticarcillin[P] | $\geq$128 | | $\leq$64 |
| Ticarcillin/K Clavulanate[E] | $\geq$128 | 32–64 | <16 |
| Ticarcillin/K Clavulanate[P] | $\geq$128 | | $\leq$64 |

[E]Enterobacteriaceae only
[P]Pseudomonas only

For these experiments with *P. aeruginosa*, the following procedure was performed: The organism was streaked onto TSA plates (Remel, Lenexa, Kans.) and incubated for 18–24 hours overnight. Well-isolated colonies from the plates were emulsified in 3 ml of sterile Inoculum Water (catalog no. B1015-2, MicroScan® system, Dade Microscan, West Sacramento, Calif.) to a final turbidity equivalent to 0.5 McFarland Barium Sulfate standard. This cell suspension was vortexed for 2 to 3 seconds and 100 $\mu$l was transferred to glass tubes containing 25 ml of Inoculum Water with Pluronic-D (catalog no. B1015-7, MicroScan® system, Dade Microscan, West Sacramento, Calif.) (hereinafter "Pluronic Inoculum Water"), or 25 ml of Pluronic Inoculum Water into which rBPI$_{21}$ in 0.2% PLURONIC P123, 0.002% TWEEN 80, 5 mM sodium citrate, 150 mM NaCl ("rBPI$_{21}$/P123") had been diluted to 64 $\mu$g/ml rBPI$_{21}$.

The 25 ml of this inoculum containing rBPI$_{21}$ was mixed by inversion and poured into a tray. The inoculum was drawn up into a manual 96-well pipetting system (RENOK™ rehydrator-inoculator system, Dade Microscan, West Sacramento, Calif.) designed for use with the Microscan® panel plates, and 110 $\mu$l of the inoculum was delivered to each well of a Microscan® MIC Plus Type 2 panel plate. When added to the wells, this inoculum achieves a final bacterial concentration of 4×10$^5$ to 7×10$^5$ CFU/ml. The panel plates were then incubated at 35° C. for 15–24 hours and read visually for cell growth.

No growth was defined as a slight whiteness in the well or a clear broth. Growth appeared as turbidity which could take the form of a white haze throughout the well, a white button in the center of the well, or a fine granule growth throughout the well. All wells were read against a black indirectly lighted background. Visual results of the biochemical reactions were read into a database for bacterial identification. The MICs for each antibiotic tested were determined by identifying the lowest concentration of antibiotic which inhibited visible growth.

Table 17 below displays a summary of the results of the antibiotic screening panel. The antibiotic susceptibility standards, which are the interpretation of an MIC as resistant, intermediate or susceptible according to Microscan®'s NCCLS-derived standards, are indicated in Table 16 as superscripts R, I and S, respectively. These data show that EDTA further enhanced the anti-bacterial activity of the rBPI$_{21}$/P123 formulation by reversing resistance of the tested *P. aeruginosa* strain to cefonicid, cefotetan, cefamandole, chloramphenicol, ampicillin/sulbactam, and amoxicillin/k clavulanate, and by increasing the susceptibility of the tested *P. aeruginosa* strain to ceftizoxime, cefotaxime, ceftriaxone, and aztreonam.

TABLE 17

Effects Of rBPI$_{21}$/P123 Formulation ± Antibiotics On
P. aeruginosa (ATCC 19660) with
varying concentrations of EDTA

| Antibiotic Tested | Control (No BPI$_{21}$) | With 0% EDTA | With 0.01% EDTA | With 0.05% EDTA | With 0.1% EDTA |
|---|---|---|---|---|---|
| Ceftizoxime | 32$^I$ | 16$^I$ | <2$^S$ | 8$^S$ | <2$^S$ |
| Ceftazidime | 2$^S$ | <1$^S$ | <1$^S$ | <1$^S$ | <1$^S$ |
| Cefotaxime | 32$^I$ | 16$^I$ | 4$^S$ | <2$^S$ | <2$^S$ |
| Ceftriaxone | 16$^I$ | 4$^S$ | 8$^S$ | <2$^S$ | <2$^S$ |
| Cefoperazone | <4$^S$ | <4$^S$ | <4$^S$ | <4$^S$ | <4$^S$ |
| Cefonicid | >16$^R$ | >16$^R$ | <2$^S$ | <2$^S$ | <2$^S$ |
| Cefotetan | >32$^R$ | >32$^R$ | <4$^S$ | <4$^S$ | <4$^S$ |
| Netilmicin | 4$^S$ | <2$^S$ | <2$^S$ | <2$^S$ | <2$^S$ |
| Cefamandole | >32$^R$ | >32$^R$ | >32$^R$ | >32$^R$ | <4$^S$ |
| Chloramphenicol | >16$^R$ | 8$^S$ | 16$^I$ | <2$^S$ | <2$^S$ |
| Ticarcillin | <16$^S$ | <16$^S$ | <16$^S$ | <16$^S$ | <16$^S$ |
| Azlocillin | <64$^S$ | <64$^S$ | <64$^S$ | <64$^S$ | <64$^S$ |
| Imipenem | 1$^S$ | 1$^S$ | <0.5$^S$ | <0.5$^S$ | <0.5$^S$ |
| Amp/Sulbact | >32$^R$ | >32$^R$ | <1$^S$ | 16$^I$ | 16$^I$ |
| Aztreonam | 4$^S$ | 4$^S$ | <1$^S$ | 2$^S$ | <1$^S$ |
| Amox/K Clavulanate | >32$^R$ | >32$^R$ | <1$^S$ | 32$^R$ | <1$^S$ |
| Ciprofloxacin | <0.25$^S$ | <0.25$^S$ | <0.25$^S$ | <0.25$^S$ | <0.25$^S$ |
| Ticar/K Clavulanate | <16$^S$ | <16$^S$ | <16$^S$ | <16$^S$ | <16$^S$ |
| Mezlocillin | <16$^S$ | <16$^S$ | <16$^S$ | <16$^S$ | <16$^S$ |
| Carbenicillin | 32$^I$ | <16$^S$ | <16$^S$ | <16$^S$ | <16$^S$ |

EXAMPLE 7

ANTI-BACTERIAL ACTIVITY OF COMPOSITIONS CONTAINING BPI PROTEIN PRODUCT AND POLOXAMER 188 OR POLOXAMER 403 ON PSEUDOMONAS INFECTION IN A RABBIT CORNEAL ULCERATION MODEL

The anti-bacterial activity of therapeutic compositions comprising BPI protein products with a poloxamer surfactant was evaluated in the context of administration both prior to and after Pseudomonas infection in a corneal infection/ulceration rabbit model.

For these experiments, the infectious organism was a strain of Pseudomonas aeruginosa 19660 obtained from the American Type Culture Collection (ATCC, Rockville, Md.). The freeze dried organism was resuspended in nutrient broth (Difco, Detroit, Mich.) and grown at 37° C. with shaking for 18 hours. The culture was centrifuged following the incubation in order to harvest and wash the pellet. The washed organism was Gram stained in order to confirm purity of the culture. A second generation was cultured using the same techniques as described above. Second generation cell suspensions were diluted in nutrient broth and adjusted to an absorbance of 1.524 at 600 nm, a concentration of approximately 6.55×10$^9$ CFU/ml. A final 1.3×10$^6$ fold dilution in nutrient broth yielded 5000 CFU/mL or 1.0×10$^2$ CFU/0.02 mL. Plate counts for CFU determinations were made by applying 100 μL of the diluted cell suspension to nutrient agar plates and incubating them for 24–48 hours at 37° C.

The animals used were New Zealand White rabbits, maintained in rigid accordance to both SERI guidelines and the ARVO Resolution on the Use of Animals in Research. A baseline examination of all eyes was conducted prior to injection in order to determine ocular health. All eyes presented with mild diffuse fluorescein staining, characteristically seen in the normal rabbit eye. The health of all eyes fell within normal limits. Rabbits weighing between 2.5 and 3.0 kg were anesthetized by intramuscular injection of 0.5–0.7 mL/kg rodent cocktail (100 mg/mL ketamine, 20 mg/mL xylazine, and 10 mg/mL acepromazine). One drop of proparacaine hydrochloride (0.5% Ophthaine, Bristol-Myers Squibb) was applied to the eye prior to injection. Twenty microliters of bacterial suspension (1×10$^2$ CFU) prepared as described above was injected into the central corneal stroma of a randomly assigned eye while the other eye remained naive. Injections, simulating perforation of the corneal epithelium, were performed using a 30-gauge ½-inch needle and a 100 μL syringe.

For the first series of experiments, a 5-day dosing regimen of BPI protein product (test drug) was as follows: on Day 0 of the study, 40 μL of test drug or vehicle control was delivered to the test eye at 2 hours (−2) and 1 hour (−1) prior to intrastromal bacterial injection (time 0), then at each of the following 10 hours (0 through +9 hrs) post-injection for a total of 12 doses (40 μL/dose); on each of Days 1–4 of the study, 40 μL of test drug or vehicle control was delivered to the test eye at each of 10 hours (given at the same time each day, e.g., 8 am–5 pm). For these experiments, to test the poloxamer 188-containing therapeutic composition, 5 animals were treated with rBPI$_{21}$ (2 mg/mL in 5 mM citrate, 150 mM NaCl, 0.2% poloxamer 188, 0.002% polysorbate 80) and 5 with buffered vehicle, and to test the poloxamer 403-containing therapeutic composition, 5 animals were treated with rBPI$_{21}$ (2 mg/mL in 5 mM citrate, 150 mM NaCl, 0.2% poloxamer 403, 0.002% polysorbate 80) and 5 animals with placebo (5 mM citrate, 150 mM NaCl, 0.2% poloxamer 403, 0.002% polysorbate 80).

Eye examinations were conducted two times each day for each 5-day study via slit lamp biomicroscopy to note clinical manifestations. Conjunctival hyperemia, chemosis and tearing, mucous discharge were graded. The grading scale for hyperemia was: 0 (none); 1 (mild); 2 (moderate); and 3 (severe). The scale for grading chemosis was: 0 (none); 1 (visible in slit lamp); 2 (moderate separation); and 3 (severe ballooning). The scale for grading mucous discharge was: 0 (none) 1 slight accumulation); 2 (thickened discharge); and 3 (discrete strands). Photophobia was recorded as present or absent. Tearing was recorded as present or absent. The corneal ulcer, when present, was assessed with respect to height (mm), width (mm), and depth (% of corneal thickness). Neovascularization was graphed with respect to the affected corneal meridians. Photodocumentation was performed daily as symptoms progressed throughout the experimental procedure.

At the completion of the 5-day study period, all rabbits were sacrificed via a lethal dose of sodium pentobarbital (6 grs/mL). Corneas were harvested and fixed in half-strength Karnovsky's fixative. The corneas were processed for light microscopy using Gram stain to assay for the presence of microbial organisms and using hematoxylin and eosin to assay for cellular infiltrate.

Examinations were conducted at 4, 24, 28, 48, 52, 72, 76, and 96 hours after injection of Pseudomonas. The results of these examinations are reported in Table 18 for the therapeutic composition comprising $rBPI_{21}$ with poloxamer 403, which provided the most potent effects.

healthy appearing, as evidenced by the application of fluorescein dye. Vehicle treated eyes at 48 hours post infection displayed severe hyperemia, chemosis and mucous discharge were present; some corneas displayed corneal melting and thinning along with an ulcerating area clouded as a result of edema, cellular infiltration and fibrin deposition. At 52 hours following injection, $rBPI_{21}$/poloxamer 403 treated eyes exhibited clear and healthy corneas which resisted staining with fluorescein, indicating that the formulation is safe and non-toxic to the corneal epithelium. In vehicle treated eyes at 52 hours post infection, sloughing of corneal epithelium was evident and while chemosis was decreasing, hyperemia was severe. In these experiments, several vehicle treated eyes presented with neovascularization, with vessels growing inward toward the central cornea. This manifestation was not noted in any $rBPI_{21}$/poloxamer 403 treated eye.

TABLE 18

Summary of Clinical Observations for therapeutic composition containing $rBPI_{21}$ and poloxamer 403

| Examination | Hyperemia* | | Chemosis* | | Mucous* | | Neovascularization | | Ulcer Size (mm) | |
|---|---|---|---|---|---|---|---|---|---|---|
| | $rBPI_{21}$ | Plbo. | $rBPI_{21}$ | Plbo. | $rBPI_{21}$ | Plbo. | $rBPI_{21}$ | Plbo. | $rBPI_{21}$ | Plbo. |
| Exam 1 4 hours | 1.2 | 1.0 | 0.2 | 0.3 | 0.5 | 0 | None | None | 1 ulcer 2 mm | 1.4 |
| Exam 2 24 hours | 0.9 | 1.6 | 0.2 | 1.0 | 0.3 | 0.5 | None | None | 1 ulcer 6 mm | 3.4 |
| Exam 3 28 hours | 0.6 | 1.7 | 0.2 | 1.1 | 0.6 | 1.3 | None | None | 1 ulcer 7 mm | 5.2 |
| Exam 4 48 hours | 0.6 | 2.4 | 0.2 | 1.3 | 0.4 | 2.1 | None | None | 1 ulcer 12 mm 1 melt | 11.4 3 melt 1 thinning |
| Exam 5 52 hours | 0.8 | 2.4 | 0.2 | 1.2 | 0.2 | 1.6 | None | Yes (1/5) | 1 ulcer 12 mm 1 melt | 11.4 3 melt 1 thinning |
| Exam 6 72 hours | 0.6 | 2.4 | 0 | 0.8 | 0.2 | 1.0 | None | Yes (1/5) | 1 ulcer 12 mm melt & thin | 11.4 4 melt 1 thinning |
| Exam 7 76 hours | 0.6 | 2.4 | 0 | 0.2 | 0.2 | 0.8 | None | Yes (2/5) | 1 ulcer 12 mm melt & thin | 11.4 4 melt 3 thinning |
| Exam 8 96 hours | 0.6 | 2.4 | 0 | 0.2 | 0.2 | 0.8 | None | Yes (2/5) | 1 ulcer 12 mm melt & thin | 11.4 4 melt 3 thinning |

*Mean scores of clinical observations graded on a scale of 0 (none) to 3 (severe).

The results set out in Table 18 reveal that treatment of the eye prior to and after perforation injury and injection of Pseudomonas provided substantial benefits in terms of reduced hyperemia, chemosis and mucous formation, as well as reduction in incidence of neovascularization along with reduced incidence and severity of corneal ulceration. At four hours after Pseudomonas injection, fluorescein staining of the cornea in both treated and control animals revealed small areas of staining consistent with the injection (puncture) injury. At 28 hours after injection, the $rBPI_{21}$/poloxamer 403 treated eye evidenced clear ocular surfaces and typically were free of evidence of hyperemia, chemosis and mucous discharge while the vehicle treated eyes showed clouding of the ocular surface resulting from corneal edema and infiltration of white cells. Iritis was conspicuous in the vehicle treated eyes at 28 hours after injection and fluorescein dye application typically revealed areas of devitalized epithelium; severe hyperemia and moderate to severe chemosis and mucous discharge were additionally noted. At 48 hours after injection, mild hyperemia was sometimes noted in the $rBPI_{21}$/poloxamer 403 treated eyes but mucous discharge and chemosis were absent; the $rBPI_{21}$/poloxamer 403 treated corneas were otherwise typically clear and Pathohistological evaluation of the $rBPI_{21}$/poloxamer 403 treated corneas stained with hematoxylin and eosin revealed healthy, intact corneal epithelium and stroma; the tissue was free of white cell infiltration. In contrast, evaluation of the vehicle treated corneas revealed absence of an epithelium and extensive infiltration of white cells into the corneal stroma.

Additional pathohistological evaluation of the $rBPI_{21}$/poloxamer 403 treated corneas stained with toluidine blue also revealed healthy, intact corneal epithelium and stoma, and further revealed corneal tissue free of Pseudomonas organisms. In contrast, evaluation of the vehicle treated corneas revealed rod shaped Pseudomonas organisms in the tissue and the presence of white cells advancing toward the organisms in the tissue. These results indicate effective corneal penetration of the $rBPI_{21}$/poloxamer 403 and effective sterilization of the tissue without neovascularization.

The $rBPI_{21}$/poloxamer 403 therapeutic composition tested in these experiments achieved the most dramatic beneficial antimicrobial and anti-angiogenic effects when compared with those of the $rBPI_{21}$/poloxamer 188 therapeutic composition tested in this severe Pseudomonas injury/infection rabbit model. Benefits in terms of suppression of neovascularization were noted for treatment with the rBPI$_{21}$/poloxamer 188 composition and no significant effects in reduction of hyperemia, chemosis, mucous formation and tearing were noted. The contrast in efficacy of the BPI$_{21}$/poloxamer 403 composition with the lesser efficacy of the rBPI$_{21}$/poloxamer 188 composition in these experiments suggested that formulation components, dosage and dosage regimen may all have a significant role in optimizing beneficial effects associated with methods according to the invention.

EXAMPLE 8
BACTERIAL AND FUNGAL GROWTH-INHIBITORY ACTIVITY OF COMPOSITONS CONTAINING BPI PROTEIN PRODUCT AND POLOXAMER 188 OR POLOXAMER 403 IN THE PRESENCE OR ABSENCE OF EDTA

The antimicrobial preservative effectiveness of therapeutic compositions comprising BPI protein product and poloxamer surfactant were evaluated according to the U.S. Pharmacopeia (USP) microbiological test protocol (USP 23, [51] Antimicrobial Preservatives-Effectiveness, p. 1681) against the standard bacterial and fungal test microorganisms: *Escherichia coli* (ATCC No. 8739), *Pseudomonas aeruginosa* (ATCC No. 9027), *Staphylococcus aureus* (ATCC No. 6538), *Candida albicans* (ATCC No. 10231) and *Aspergillus niger* (ATCC No. 16404).

For these experiments, a small volume of the cultures from each of the five test microorganisms prepared according to the USP protocol was added into sterile containers with a solution of 2 mg/ml rBPI$_{21}$, 0.2% poloxamer 188 (PLURONIC F68) or poloxamer 403 (PLURONIC P123), 0.002% TWEEN 80, 5 mM sodium citrate and 150 mM sodium chloride. In some experiments, these solutions additionally contained various concentrations of EDTA. Aliquots of test solution were removed from the containers at various time periods after inoculation with the microorganisms (i.e., 7, 14, 21, and 28 days) and plated to determine the number of colony forming units (CFU) of each of the five microorganisms. According to USP standards, the product shows effectiveness if (a) the concentrations of viable bacteria are reduced to not more than 0.1% of the initial concentrations by the fourteenth day; (b) the concentrations of viable fungi remain at or below the initial concentrations during the first 14 days; and (c) the concentration of each test microorganism remains at or below these designated levels during the remainder of the 28-day test period.

The results of initial testing of rBPI$_{21}$/poloxamer 188 and rBPI$_{21}$/poloxamer 403 compositions are shown in Tables 19A–19B below.

TABLE 19A

CFUs after incubation with 2 mg/mL rBPI$_{21}$/0.2% poloxamer 188

| Organisms | Initial | 7 Day | 14 Day | 21 Day | 28 Day |
|---|---|---|---|---|---|
| E. coli | $4.9 \times 10^6$ | $1.67 \times 10^3$ | $6.7 \times 10^2$ | <1 | <1 |
| P. aeruginosa | $1.46 \times 10^6$ | $1.7 \times 10^2$ | $5.8 \times 10^3$ | $4.7 \times 10^4$ | $2.05 \times 10^5$ |
| S. aureus | $3.6 \times 10^6$ | $7.5 \times 10^2$ | $7.5 \times 10^1$ | $2.9 \times 10^2$ | $1.15 \times 10^3$ |
| C. albicans | $3.3 \times 10^6$ | $2.62 \times 10^6$ | $2.62 \times 10^6$ | $2.96 \times 10^6$ | $4.1 \times 10^6$ |
| A. niger | $5.5 \times 10^5$ | $8.5 \times 10^5$ | $6.9 \times 10^5$ | $2.6 \times 10^5$ | $7.1 \times 10^5$ |

TABLE 19B

CFUs after incubation with 2 mg/mL rBPI$_{21}$/0.2% poloxamer 403

| Organisms | Initial | 7 Day | 14 Day | 21 Day | 28 Day |
|---|---|---|---|---|---|
| E. coli | $7.2 \times 10^5$ | 0 | 0 | 0 | 0 |
| P. aeruginosa | $1.02 \times 10^5$ | 0 | 0 | 0 | 0 |
| S. aureus | $6.2 \times 10^5$ | $1.8 \times 10^1$ | 0 | 0 | 0 |
| C. albicans | $3.4 \times 10^5$ | $1 \times 10^5$ | $7.4 \times 10^4$ | $7.9 \times 10^4$ | $7.9 \times 10^4$ |
| A. niger | $1.9 \times 10^5$ | $1.5 \times 10^5$ | $1.4 \times 10^5$ | $1.4 \times 10^5$ | $8.9 \times 10^4$ |

When additional compositions of rBPI$_{21}$/poloxamer 403 as described above were prepared with concentrations of 0.01%, 0.05% and 0.1% EDTA and tested in the experiments shown in Table 19B above, the results obtained were comparable to those shown in Table 19B above for all organisms.

In additional experiments, other compositions of 2 mg/mL rBPI$_{21}$, 0.2% PLURONIC P123, 0.002% TWEEN 80, 5 mM sodium citrate, 150 mM sodium chloride with and without 0.05% EDTA were evaluated for effectiveness as described above. The results are shown in Table 20 below. In these experiments, 0.05% EDTA further enhanced the antimicrobial effectiveness of the rBPI$_{21}$/poloxamer 403 composition.

TABLE 20

| | | CFUs after incubation with 2 mg/mL rBPI$_{21}$/0.2% poloxamer 403 ± 0.05% EDTA | | | | | | |
|---|---|---|---|---|---|---|---|---|
| | | 7 Day | | 14 Day | | 21 Day | | 28 Day | |
| Organisms | Initial | −EDTA | +EDTA | −EDTA | +EDTA | −EDTA | +EDTA | −EDTA | +EDTA |
| E. coli | $1.97 \times 10^5$ | 10 | 1 | 1 | 1 | 1 | 1 | 1 | 1 |
| P. aeruginosa | $7 \times 10^4$ | 1 | 1 | 1 | 1 | 1 | 1 | 1 | 1 |
| S. aureus | $9.4 \times 10^4$ | 1 | $3.9 \times 10^3$ | 1 | 1 | 1 | 1 | 1 | 1 |
| C. albicans | $3 \times 10^3$ | $8.8 \times 10^3$ | $1.5 \times 10^3$ | $1.45 \times 10^4$ | $3 \times 10^2$ | $4.1 \times 10^4$ | $3.4 \times 10^2$ | $5 \times 10^5$ | $1.7 \times 10^2$ |
| A. niger | $7.25 \times 10$ | $1.8 \times 10^4$ | $1.2 \times 10^4$ | $4.1 \times 10^4$ | $5.7 \times 10^4$ | $1.69 \times 10^4$ | $4.4 \times 10^4$ | $1.4 \times 10^4$ | $1.66 \times 10^4$ |

Numerous modifications and variations of the above-described invention are expected to occur to those of skill in the art. Accordingly, only such limitations as appear in the appended claims should be placed thereon.

What is claimed are:

1. A composition comprising (a) a BPI protein product, (b) a polyoxypropylene-polyoxyethylene block copolymer (poloxamer) surfactant selected to enhance the anti-bacterial activity of the BPI protein product, and (c) EDTA.

2. A composition comprising a BPI protein product, and a poloxamer surfactant selected to enhance the anti-bacterial activity of the BPI protein product, wherein the poloxamer surfactant is selected from the group consisting of poloxamer 333, poloxamer 334, and poloxamer 335.

3. The composition of claim 2 further comprising EDTA.

4. A composition comprising (a) a BPI protein product, (b) a poloxamer surfactant selected to enhance the bacterial or fungal growth-inhibiting activity of the BPI protein product, and (c) EDTA.

5. A composition comprising a BPI protein product and a poloxamer surfactant selected to enhance the bacterial or fungal growth-inhibiting activity of the BPI protein product, wherein the poloxamer surfactant is selected from the group consisting of poloxamer 333, poloxamer 334, and poloxamer 335.

6. The composition of claim 5 further comprising EDTA.

* * * * *